(12) United States Patent
Collard et al.

(10) Patent No.: US 10,435,690 B2
(45) Date of Patent: Oct. 8, 2019

(54) TREATMENT OF ALPHA-L-IDURONIDASE (IDUA) RELATED DISEASES BY INHIBITION OF NATURAL ANTISENSE TRANSCRIPT TO IDUA

(71) Applicant: CuRNA, Inc., Miami, FL (US)

(72) Inventors: Joseph Collard, Delray Beach, FL (US); Olga Khorkova Sherman, Tequesta, FL (US); Carlos Coito, West Palm Beach, FL (US); Gang Shen, Andover, MA (US)

(73) Assignee: CuRNA, Inc., Miami, FL (US)

( * ) Notice: Subject to any disclaimer, the term of this patent is extended or adjusted under 35 U.S.C. 154(b) by 0 days.

(21) Appl. No.: 15/847,283

(22) Filed: Dec. 19, 2017

(65) Prior Publication Data

US 2018/0135050 A1    May 17, 2018

Related U.S. Application Data

(62) Division of application No. 14/925,196, filed on Oct. 28, 2015, now Pat. No. 9,873,873, and a division of application No. 13/880,409, filed as application No. PCT/US2011/057097 on Oct. 20, 2011, now Pat. No. 9,222,088.

(60) Provisional application No. 61/405,758, filed on Oct. 22, 2010.

(51) Int. Cl.
| | |
|---|---|
| *C12N 15/113* | (2010.01) |
| *A61K 31/7088* | (2006.01) |
| *C12N 15/10* | (2006.01) |
| *G01N 33/53* | (2006.01) |

(52) U.S. Cl.
CPC ........ *C12N 15/113* (2013.01); *A61K 31/7088* (2013.01); *C12N 15/1034* (2013.01); *C12Y 302/01076* (2013.01); *G01N 33/5308* (2013.01); *C12N 2310/11* (2013.01); *C12N 2310/113* (2013.01); *C12N 2310/315* (2013.01); *C12N 2310/321* (2013.01); *C12N 2310/322* (2013.01); *C12N 2320/50* (2013.01)

(58) Field of Classification Search
CPC .............. C12N 15/113; C12N 2310/11; A61K 31/7088
See application file for complete search history.

(56) References Cited

U.S. PATENT DOCUMENTS

| | | | | |
|---|---|---|---|---|
| 6,159,946 | A * | 12/2000 | Zalewski | A61K 31/70 435/375 |
| 6,238,662 | B1 * | 5/2001 | Scott | C12Y 302/0107 424/94.61 |
| 6,528,262 | B1 * | 3/2003 | Gilad | C12N 15/113 435/6.16 |
| 2003/0143606 | A1 * | 7/2003 | Olek | C07K 14/4703 435/6.12 |
| 2004/0132063 | A1 * | 7/2004 | Gierse | C12N 15/1137 435/6.14 |
| 2005/0153924 | A1 * | 7/2005 | Bennett | C12N 15/1138 514/44 A |
| 2007/0054278 | A1 * | 3/2007 | Cargill | C12Q 1/6827 435/6.11 |
| 2007/0178458 | A1 * | 8/2007 | O'Brien | C07H 21/04 435/6.14 |
| 2010/0105760 | A1 * | 4/2010 | Collard | C07K 14/775 514/44 A |

OTHER PUBLICATIONS

Wahlestedt et al. Drug Discovery Today 11: 503-508 (Year: 2006).*
Chitsaz et al. Bioinformatics 25: ISMB i365-i373 (Year: 2009).*
Tolar et al. Biologics: Targets & Therapy 2008: 2: 743-751 (Year: 2008).*
LIB3184-008-P2-K1-C2 LIB3184 Canis lupus familaris cDNA clone CLN1560395, mRNA sequence GenBank retrieved on Sep. 17, 2018 from http://www.ncbi.nlm.nih.gov/nucest/DN330918 (Year: 2005).*

* cited by examiner

*Primary Examiner* — Brian Whiteman
(74) *Attorney, Agent, or Firm* — CuRNA, Inc.; Monte E. Browder

(57) ABSTRACT

The present invention relates to antisense oligonucleotides that modulate the expression of and/or function of Alpha-L-Iduronidase (IDUA), in particular, by targeting natural antisense polynucleotides of Alpha-L-Iduronidase (IDUA). The invention also relates to the identification of these antisense oligonucleotides and their use in treating diseases and disorders associated with the expression of IDUA.

8 Claims, 3 Drawing Sheets

Specification includes a Sequence Listing.

(SEQ ID NO: 8)

SEQUENCE LISTING

<160> NUMBER OF SEQ ID NOS: 45

<210> SEQ ID NO 1
<211> LENGTH: 2203
<212> TYPE: DNA
<213> ORGANISM: Homo sapiens

<400> SEQUENCE: 1

```
gtcacatggg gtgcgcgccc agactccgac ccggaggcgg aaccggcagt gcagcccgaa      60
gccccgcagt ccccgagcac gcgtggccat gcgtcccctg cgccccgcg  ccgcgctgct     120 ggcgctcctg gcctcgctcc tggccgcgcc cccggtggcc ccggccgagg ccccgcacct     180
```

```
ggtgcatgtg gacgcggccc gcgcgctgtg gccccctgcgg cgcttctgga ggagcacagg    240
cttctgcccc ccgctgccac acagccaggc tgaccagtac gtcctcagct gggaccagca    300
gctcaacctc gcctatgtgg gcgccgtccc tcaccgcggc atcaagcagg tccggaccca    360
ctggctgctg gagcttgtca ccaccagggg gtccactgga cggggcctga gctacaactt    420
cacccacctg gacgggtacc tggaccttct cagggagaac cagctcctcc cagggtttga    480
gctgatgggc agcgcctcgg gccacttcac tgactttgag acaagcagc aggtgtttga    540 gtggaaggac ttggtctcca gcctggccag agatacatc ggtaggtacg gactggcgca    600
tgtttccaag tggaacttcg agacgtgaa tgagccagac caccacgact ttgacaacgt    660
ctccatgacc atgcaaggct tcctgaacta ctacgatgcc tgctcggagg gtctgcgcgc    720
cgccagcccc gccctgcggc tgggaggccc cggcgactcc ttccacaccc caccgcgatc    780
cccgctgagc tggggcctcc tgcgccactg ccacgacggt accaacttct tcactgggga    840
ggcgggcgtg cggctggact acatctccct ccacaggaag ggtgcgcgca gctccatctc    900
catcctggag caggagaagg tcgtcgcgca gcagatccgg cagctcttcc ccaagttcgc    960
ggacaccccc atttacaacg acgaggcgga cccgctggtg ggctggtccc tgccacagcc    1020
gtggagggcg gacgtgacct acgcggccat ggtggtgaag gtcatcgcgc agcatcagaa    1080
cctgctactg gccaacacca cctccgcctt ccctacgcg ctcctgagca acgacaatgc    1140
cttcctgagc taccacccgc accccttcgc gcagcgcacg ctcaccgcgc gcttccaggt    1200
caacaacacc cgcccgccgc acgtgcagct gttgcgcaag ccggtgctca cggccatggg    1260
gctgctggcc ctgctggatg aggagcagct ctgggccgaa gtgtcgcagg ccgggaccgt    1320
cctggacagc aaccacacgg tgggcgtcct ggccagcgcc caccgccccc agggcccggc    1380
cgacgcctgg cgcgccgcgg tgctgatcta cgcgagcgac gacacccgcg cccaccccaa    1440
ccgcagcgtc gcggtgaccc tgcggctgcg cggggtgccc cccggcccgg cctggtcta    1500 cgtcacgcgc tacctggaca acgggctctg cagccccgac ggcgagtggc ggcgcctggg    1560
ccggcccgtc ttccccacgg cagagcagtt ccggcgcatg cgcgcggctg aggacccggt    1620
ggccgcggcg ccccgcccct taccgccgg cggccgcctg accctgcgcc ccgcgctgcg    1680
gctgccgtcg cttttgctgg tgcacgtgtg tgcgcgcccc gagaagccgc ccgggcaggt    1740
cacgcggctc cgcgccctgc ccctgaccca agggcagctg gttctggtct ggtcggatga    1800
acacgtgggc tccaagtgcc tgtggacata cgagatccag ttctctcagg acggtaaggc    1860
gtacaccccg gtcagcagga agccatcgac cttcaacctc tttgtgttca gcccagacac    1920
aggtgctgtc tctggctcct accgagttcg agccctggac tactgggccc gaccaggccc    1980
cttctcggac cctgtgccgt acctggaggt ccctgtgcca agagggcccc catccccggg    2040
caatccatga gcctgtgctg agcccagtg ggttgcacct ccaccggcag tcagcgagct    2100
ggggctgcac tgtgcccatg ctgccctccc atcaccccct ttgcaatata tttttatatt    2160 ttattattt ctttatatc ttggtaaaaa aaaaaaaaaa aaa                        2203
```

<210> SEQ ID NO 2
<211> LENGTH: 2695
<212> TYPE: DNA
<213> ORGANISM: Homo sapiens

<400> SEQUENCE: 2

```
tcggcagggc ttggagcccc gcttccttgc gggcctcagg ggctgctctg aggaccgatg     60
actcggaaag cgctcagaag aacgcttcgc ccgttggtgc tatgtgagtt gagccattac    120
```

```
tgtcttgttt  ttctctgttt  ttgtgtgttt  ttgagacaga  gtcttgcttt  gtcgcccagg    180
ctgaggtgca  gtggcgcgat  ctcagctcac  tgcaacctcc  atctccgggg  cttcagcgat    240
tttctcaccc  cagcctcctg  agtaaagcgt  gcgctttagc  aggaaggaga  attacccag     300 aagagcacac  tgggccctcc  ttacacttgg  cttcagatcc  atggattcaa  ccaagcagac    360
tgaaaatatt  gttttaaagc  caaagcaata  cgaataata   catattttaa  aacaatacag    420
tataacagct  atttcagag   catttacatt  gttttaggga  ctataagtaa  tcttgattta    480
aactacacag  taggatgtgc  gtaggtaatg  tgcaaatact  gtgccatttt  atatcaagta    540
cttgagcacc  tgcaaatttt  ggtatctggg  agggtcctgg  aaccaatacc  ccgaggatac    600
catgggacaa  ctgtagtaca  tgtgtagtcc  atgtatgcat  gtgtgaatcc  aagcaaacat    660
tgtataaaaa  taataatgga  agaacaggc   ttggtgcggt  ggctcacacc  tgcaatccca    720
gcactttgga  attgcaggcc  aacacgggag  gatcacttga  ggcctggagt  ttgaaatcgg    780
cctgggagat  gtaccaagac  ccatctgta   caaaaaaaa   aatttagcca  gatgcgatgg    840
tatatgcctg  tgaggcccag  ctacccacga  aattgaggtg  ggagattgct  tgagcttagg    900
agttcaaggc  tgagacgggc  catgatcaca  ccactacatt  ccagcctggt  tgacaaaatg    960
agaccccatc  tctaaaaaaa  gaagagaaaa  aagaacagt   ctactaacaa  aacgaaaata   1020
ctggacaata  atcctctcta  agttgggaga  aggataatta  gagttacagt  gttctgggtc   1080 ttttatttt   ggggagaggg  gttaaaatat  tgcttaacat  taggtcttct  tatgttgaaa   1140
ttgcattaaa  agtgattagc  catttaaaag  tgaaatagtg  tgtatatatt  ccaaattagc   1200
aaggaggaaa  aacataatac  aaaaaaattc  attaagaaac  taaaaagtaa  gaaagggagg   1260
gaaaggcgag  agaaaccatg  caagtacaga  actgtctcca  ggaacagcgg  ggtaagaccc   1320
tcagtccaac  gaccccagag  aaaacaacta  aaatgatgga  taactcgctt  taaaaacaat   1380
tcctcaaagc  gtcagagaac  tgagaaaaac  agtaagaaac  caccagtccc  acaccgtggt   1440
gcaggacaca  gcaatggaaa  ctgaattgtt  tcagaccagc  cgcctcctga  gagcaaccat   1500
cagaactgga  gagcgctgca  cggaaccgtc  cagggcactg  ggagctctga  ggagcctctg   1560
aggcctcggg  gctctgcagg  gacaagccgg  gaggggggcgg  ggcccgcttt  ggggcggcga   1620
ctccacaccc  ctgcagcgta  tcccagccac  acaagacatg  gcgacacgct  gctgcgttcg   1680
ttcctcacac  tgtggccaca  ggacagaagt  cgaggctcag  gcgggggggcc  tggtaaagac   1740 tttgggtttt  tcttgggacc  ccaaagttct  atccctaaa   agcaaaggta  aaccagcaac   1800
agaattgtct  ttgtggggac  tgaagccagc  cttaaatcac  ctcaagccct  gagagaatta   1860
aggtgagccg  ctcaccggga  cacctgtgga  cagaaaagta  caccttccct  ggaggaaggt   1920
aaaacaaaac  aaaaacagac  agaagtcctc  actgcacggt  gctggaatgg  atccgggtca   1980
ggaaaaatta  ttacaaagtg  catgatgggg  acattcacaa  tttggaatat  gccttgtaca   2040
ttgtgcaaca  aaattctacc  aatgataaac  tccagaattt  tttttgtttt  tgttttttgt   2100
ttttttaaac  gaagtctcac  tctgttgtcc  aggctggagt  gcagtggtgt  gatctcagct   2160
cattgcaacc  tctgcctcag  cctcctgagt  agctgggatt  acaggcatga  gccaccacgc   2220
ccagccaatt  tttgtatttt  cggtagagac  agcgttttac  catcctggcc  aggctggtct   2280
cgacctcctg  acctcgaatg  atccacctgc  ctcggcctcc  caaagtgctg  ggattatagg   2340
catgagccac  cgcgctgggt  caaactccag  aattattaaa  cgactcaatg  attgcatcac   2400
ggttgtgaat  ggagattttt  tgttcatttg  tgatccatgc  tgaagggttt  agaggtgaag   2460
aatcaataga  tttgtaacca  aagttgctct  ggaaattaaa  gcaaaacaat  aaatttagat   2520
```

| | |
|---|---:|
| tacatacaga gactgagata aaagcaaagg tagcaaaata ttaacagttg gtgaacctgg | 2580 |
| gtgaaaacta tatactgtta ttgcaacttt tctgtgagtt tgagattttt caaaatgaaa | 2640 |
| acattgaaaa aaatattaaa acctcatgaa acttagtaaa aatttattga atgat | 2695 |

<210> SEQ ID NO 3
<211> LENGTH: 2082
<212> TYPE: DNA
<213> ORGANISM: Homo sapiens

<400> SEQUENCE: 3

| | |
|---|---:|
| gggagggggtt gggtggcctc ggggagcctc ggggagccgg gagcacggca gggcttggag | 60 |
| ccccgcttcc ttgcgggcct caggggctgc tctgaggacc gatgactcgg aaagcgctca | 120 |
| gaagaacgct tcgcccgttg gtgctatgtg agttgagcca ttactgtctt gtttttctct | 180 |
| gttttgtgt gtttttgaga cagagtcttg ctttgtcgcc caggctgagg tgcagtggcg | 240 |
| cgatctcagc tcactgcaac ctccatctcc ggggcttcag cgattttctc accccagcct | 300 |
| cctgagtaaa gcgtgcgctt tagcaggaag agaattacc ccagaagagc acactgggcc | 360 |
| ctccttacac ttggcttcag atccatggat tcaaccaagc agactgaaaa tattgtttta | 420 |
| aagccaaagc aatacgaaat aatacatatt taaaacaat acagtataac agctatttac | 480 |
| agagcattta cattgtttta gggactataa gtaatcttga tttaaactac acagtaggat | 540 |
| gtgcgtaggt aatgtgcaaa tactgtgcca ttttatatca agtacttgag cacctgcaaa | 600 |
| ttttggtatc tgggagggtc ctggaaccaa taccccgagg ataccatggg acaactgtag | 660 |
| tacatgtgta gtccatgtat gcatgtgtga atccaagcaa acattgtata aaaataataa | 720 |
| tggaaagaac aggcttggtg cggtggctca cacctgcaat cccagcactt tggaattgca | 780 |
| ggccaacacg ggaggatcac ttgaggcctg gagtttgaaa tcggcctggg agatgtacca | 840 |
| agacccatc tgtacaaaaa aaaatttag ccagatgcga tggtatatgc ctgtgaggcc | 900 |
| cagctaccca cgaaattgag gtgggagatt gcttgagctt aggagttcaa ggctgagacg | 960 |
| ggccatgatc acaccactac attccagcct ggttgacaaa atgagacccc atctctaaaa | 1020 |
| aaagaaaaga aaaaagaac agtctactaa caaaacgaaa atactggaca ataatcctct | 1080 |
| ctaagttggg agaaggataa ttagagttac agtgttctgg gtctttttat tttggggaga | 1140 |
| ggggttaaaa tattgcttaa cattaggtct tcttatgttg aaattgcatt aaaagtgatt | 1200 |
| agccatttaa aagtgaaata gtgtgtatat attccaaatt agcaaggagg aaaaacataa | 1260 |
| tacaaaaaaa ttcattaaga aactaaaaag taagaaaggg agggaaaggc gagagaaacc | 1320 |
| atgcaagtac agaactgtct ccaggaacag cggggtaaga ccctcagtcc aacgaccccca | 1380 |
| gagaaaacaa ctaaaatgat ggataactcg ctttaaaaac aattcctcaa agcgtcagag | 1440 |
| aactgagaaa acagtaagaa accaccagt cccacaccgt ggtgcaggac acagcaatgg | 1500 |
| aaactgaatt gtttcagacc agccgcctcc tgagagcaac catcagaact ggagagcgct | 1560 |
| gaacggaacc gtccagggca ctgggagctc tgaggagcct ctgaggcctc ggggctctgc | 1620 |
| agggacaagc cgggaggggg cggggcccgc tttgggcgg cgactccaca cccctgcagc | 1680 |
| gtatcccagc cacacaagac atggcgacac gctgctgcgt tcgttcctca cactgtggcc | 1740 |
| acaggacaga agtcgaggct caggcggggg gcctggtaaa gactttgggt ttttcttggg | 1800 |
| accccaaagt tctatcccct aaaagcaaag gtaaaccagc aacagaattg tctttgtggg | 1860 |
| gactgaagcc agccttaaat cacctcaagc cctgagagaa ttaaggtgag ccgctcaccg | 1920 |
| ggacacctgt ggacagaaaa gtacaccttc cctggaggaa ggtaaaacaa aacaaaaaca | 1980 |

```
gacagaagtc ctcactgcac ggtgctggaa tggatccggg tcaggaaaaa ttattacaaa    2040
gtgcatgatg gggacattca caatttggaa tatgccttgt ac                       2082
```

<210> SEQ ID NO 4
<211> LENGTH: 322
<212> TYPE: DNA
<213> ORGANISM: Canis lupus
<220> FEATURE:
<221> NAME/KEY: misc_feature
<222> LOCATION: (290)..(290)
<223> OTHER INFORMATION: n is a, c, g, or t

<400> SEQUENCE: 4

```
cgcagccggc ggccccgcc cggccagacc cttcggcccc ggccccgccg accagcacag      60
ccgccgccgt cagggctccc gcagggacct ggggcggcca cgccgctgt cggagcagcc     120 ctcccagcac agacgcgggg tctctgcatc aggggggcatc gggggcagcc ggggccgtct   180 tcctcccctcc aagcccacgg tgcaaaggtt ttccccagag cgtggctcgc caggatggag   240
gtgtcccctg agtgcccgcg gcggggcggg gggccggtgc tggtgcgcan gcggtccccg   300
gtgcccctgg ggctgcgcga ga                                             322
```

<210> SEQ ID NO 5
<211> LENGTH: 677
<212> TYPE: DNA
<213> ORGANISM: Canis lupus

<400> SEQUENCE: 5

```
gctcggccgc attgatgccc acggagggcg gcttccacgc cgtcgtcatc gactgcgccc     60
cgctgctctt cctggatgca gccggcgtgg ctacgctgcg ggacctgcgc cgggactacg    120
gggccctgga catcaccctg ctcctggcct gctgcagccc cttggtgagg aacaccctga    180
ggagaggtgg cttcctcggg gacgaccggg ggacgcggc cgaggaggcg cagctgttcc     240
acagcgtgca tggcgccgtg caggtggccc gagcccgccg cagggaggca gcagccaccg    300
actccaccct ctagagccag cgcccgaccc cggggccccc ggcaggcagg ctccggctca    360 gtcaccgtg tccatcacct caaccctcca agcggaggct gtgccctctg gcctggggga    420
gccagggagc acacagggac ccaggcccgt tgaagtcaag agcttcaaca gtggtcttgc    480
aagtcaacgt gacgccgggt gtcaccgtct tatttgaaca agggcccga cgtggtcagg    540 atgcctccca ggtgccaatc gggtactggt cccttggcct gtcccgtgcc agtcccaccg    600
cggccggggg tgcgaggatc tctgtgtctc tggacttcca aacacacccc tgggtgtccc    660
ctatgcctgc agcctgc                                                   677
```

<210> SEQ ID NO 6
<211> LENGTH: 716
<212> TYPE: DNA
<213> ORGANISM: Canis lupus
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (9)..(21)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (44)..(46)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t
<220> FEATURE:
<221> NAME/KEY: misc_feature
<222> LOCATION: (69)..(70)
<223> OTHER INFORMATION: n is a, c, g, or t
<220> FEATURE:
<221> NAME/KEY: misc_feature
<222> LOCATION: (144)..(145)
<223> OTHER INFORMATION: n is a, c, g, or t
<220> FEATURE:
<221> NAME/KEY: misc_feature
<222> LOCATION: (182)..(183)
<223> OTHER INFORMATION: n is a, c, g, or t
<220> FEATURE:
<221> NAME/KEY: misc_feature
<222> LOCATION: (691)..(697)
<223> OTHER INFORMATION: n is a, c, g, or t
<220> FEATURE:
<221> NAME/KEY: misc_feature
<222> LOCATION: (703)..(707)
<223> OTHER INFORMATION: n is a, c, g, or t

<400> SEQUENCE: 6

```
acnnnntcnn nnnnnnnnnn nggtgccaat cgngtantgg tccnnnggnn tgtcccgtgn      60
nagtcccann gcggccgggg gtgcgaggat ctctgtgtct ctggacttcc aaacacaccc     120
ctgggtgtcc cctatgcctg cagnntgcag ggcagggccc ctgggccgcg ttcctccaag     180
gnntgaccgg tgagcacagg gccgggctgc gtgggtgtgt ccagccacgg agccactgca     240
ggagacacca ccttgaccct gagcccctca gtgagcccccg cggggagcca gctgtgccca    300
gtccagggcc cgcccggccc ccacacagcc tctccacgag gaacagtgga cgatgggccc    360
ccctccctcc tgcctcccgc ccacctccgc acctgacctg ccccagcctc gctctccagc    420
ccccagccgg ctctcccagc tgcccaccac tcacctggcc gtgatgagct ccagcagcca    480
gtgggtccgg acctgctcga tgccccgtg agggacagca cccacatagg ccaggttgag    540
ctgctggtcc cagctgaggt catagcggtc agcctggctg tgcggcaggg ggggctggg    600
gcagagcgag ggggcgggca ttagtgcccc cgacggcccg ggaggcccag gacgccaggc    660
tccagcagcg gcccgggcag tgcctgccaa nnnnnnntcc gcnnnnnaat aaaatg       716
```

<210> SEQ ID NO 7
<211> LENGTH: 466
<212> TYPE: DNA
<213> ORGANISM: Canis lupus

<400> SEQUENCE: 7

```
gcagctcgca ggctggcggg ttcccgcagg gccttggtgt tgctgtcagg gcagatggct      60
ccgtacagtt tgctaaagga cgacaggagg accgcagggg tcccgccacc gcagctcccc    120
gtgcttccca accaccgggg cctctgggga ggtggcgagc cttctgggat tgtggatccg    180
acaccgggac gccagggggct ggaaaacctca ggtgcgattt agccgagcgg cgagcgcatt   240
```

| | |
|---|---|
| tgtggtgttc ccagtcactt ccttgtgtcg cggcgtcaac accagtcacc ctggcacagg | 300 |
| aaacagcttc caggaacggc cctggcagtt aacccgaagg actggatcac gtggactttc | 360 |
| gcaacaggat taaacatttg ctgctttacc aggaaatgct gacaccgaga taacgtgcag | 420 |
| ccctcgcggc aacgtgaca gggacacgac ggaagaaggc tcatcc | 466 |

```
<210> SEQ ID NO 8
<211> LENGTH: 1255
<212> TYPE: DNA
<213> ORGANISM: Canis lupus

<400> SEQUENCE: 8
```

| | |
|---|---|
| gctcggccgc attgatgccc acggagggcg gcttccacgc cgtcgtcatc gactgcgccc | 60 |
| cgctgctctt cctggatgca gccggcgtgg ctacgctgcg ggacctgcgc cgggactacg | 120 |
| gggccctgga catcaccctg ctcctggcct gctgcagccc cttggtgagg aacaccctga | 180 |
| ggagaggtgg cttcctcggg gacgacccgg gggacgcggc cgaggaggcg cagctgttcc | 240 |
| acagcgtgca tggcgccgtg caggtggccc gagcccgccg cagggaggca gcagccaccg | 300 |
| actccaccct ctagagccag cgcccgaccc cggggccccc ggcaggcagg ctccggctca | 360 |
| gtcaccgtg tccatcacct caaccctcca agcggaggct gtgccctctg gcctggggga | 420 |
| gccagggagc acacagggac ccaggcccgt tgaagtcaag agcttcaaca gtggtcttgc | 480 |
| aagtcaacgt gacgccgggt gtcaccgtct tatttgaaca agggccccga cgtggtcagg | 540 |
| atgcctccca ggtgccaatc gggtactggt cccttggcct gtcccgtgcc agtcccaccg | 600 |
| cggccggggg tgcgaggatc tctgtgtctc tggacttcca aacacacccc tgggtgtccc | 660 |
| ctatgcctgc agcctgcagg gcagggcccc tgggccgcgt tcctccaagg cctgaccggt | 720 |
| gagcacaggg ccgggctgcg tgggtgtgtc cagccacgga gccactgcag gagacaccac | 780 |
| cttgaccctg agcccctcag tgagcccgc ggggagccag ctgtgcccag tccaggggcc | 840 |
| gcccggcccc cacacagcct ctccacgagg aacagtggac gatgggcccc cctccctcgt | 900 |
| gcctcccgcc cacctccgca cctgacttgc cccagcctcg ctctccagcc ccagcgggt | 960 |
| tctcccagct gcccaccact cacctggccg tgatgagctc cagcagccag tgggtccgga | 1020 |
| cctgctcgat gcccccgtga gggacagcac ccacataggc caggttgagc tgctggtccc | 1080 |
| agctgaggtc atagcggtca gcctggctgt gcggcagggg ggggctgggg cagagcgagg | 1140 |
| gggcgggcat tagtgccccc gacggcccgg gaggcccagg acgccaggct ccagcagcgg | 1200 |
| cccgggcagt gcctgccaac ccccgctccg ccccggaata aaatgacccc aagag | 1255 |

```
<210> SEQ ID NO 9
<211> LENGTH: 2739
<212> TYPE: DNA
<213> ORGANISM: Homo sapiens

<400> SEQUENCE: 9
```

| | |
|---|---|
| gggaggggtt gggtggcctc ggggagcctc ggggagccgg gagcacggca gggcttggag | 60 |
| ccccgcttcc ttgcgggcct caggggctgc tctgaggacc gatgactcgg aaagcgctca | 120 |
| gaagaacgct tcgcccgttg gtgctatgtg agttgagcca ttactgtctt gttttctct | 180 |
| gttttttgtgt gttttttgaga cagagtcttg ctttgtcgcc caggctgagg tgcagtggcg | 240 |
| cgatctcagc tcactgcaac ctccatctcc ggggcttcag cgattttctc accccagcct | 300 |
| cctgagtaaa gcgtgcgctt tagcaggaag gagaattacc ccagaagagc acactgggcc | 360 |

```
ctccttacac ttggcttcag atccatggat tcaaccaagc agactgaaaa tattgtttta    420
aagccaaagc aatacgaaat aatacatatt ttaaaacaat acagtataac agctatttac    480
agagcattta cattgtttta gggactataa gtaatcttga tttaaactac acagtaggat    540
gtgcgtaggt aatgtgcaaa tactgtgcca ttttatatca agtacttgag cacctgcaaa    600
ttttggtatc tgggagggtc ctggaaccaa taccccgagg ataccatggg acaactgtag    660
tacatgtgta gtccatgtat gcatgtgtga atccaagcaa acattgtata aaaataataa    720
tggaaagaac aggcttggtg cggtggctca cacctgcaat cccagcactt tggaattgca    780
ggccaacacg ggaggatcac ttgaggcctg gagtttgaaa tcggcctggg agatgtacca    840
agaccccatc tgtacaaaaa aaaaaattta gccagatgcg atggtatatg cctgtgaggc    900
ccagctaccc acgaaattga ggtgggagat tgcttgagct taggagttca aggctgagac    960
gggccatgat cacaccacta cattccagcc tggttgacaa aatgagaccc catctctaaa   1020
aaaagaagag aaaaaaagaa cagtctacta acaaaacgaa aatactggac aataatcctc   1080
tctaagttgg gagaaggata attagagtta cagtgttctg ggtcttttta ttttggggag   1140
agggggttaaa atattgctta acattaggtc ttcttatgtt gaaattgcat taaaagtgat   1200
tagccattta aaagtgaaat agtgtgtata tattccaaat tagcaaggag gaaaacata    1260
atacaaaaaa attcattaag aaactaaaaa gtaagaaagg gagggaaagg cgagagaaac   1320
catgcaagta cagaactgtc tccaggaaca gcggggtaag accctcagtc caacgacccc   1380
agagaaaaca actaaaatga tggataactc gctttaaaaa caattcctca aagcgtcaga   1440
gaactgagaa aaacagtaag aaaccaccag tcccacaccg tggtgcagga cacagcaatg   1500
gaaactgaat tgtttcagac cagccgcctc ctgagagcaa ccatcagaac tggagagcgc   1560
tgcacggaac cgtccagggc actgggagct ctgaggagcc tctgaggcct cggggctctg   1620
cagggacaag ccgggagggg gcggggcccg ctttggggcg gcgactccac acccctgcag   1680
cgtatcccag ccacacaaga catggcgaca cgctgctgcg ttcgttcctc acactgtggc   1740
cacaggacag aagtcgaggc tcaggcgggg ggcctggtaa agactttggg ttttcttgg   1800
gaccccaaag ttctatcccc taaaagcaaa ggtaaaccag caacagaatt gtctttgtgg   1860
ggactgaagc cagccttaaa tcacctcaag ccctgagaga attaaggtga gccgctcacc   1920
gggacacctg tggacagaaa agtacacctt ccctggagga aggtaaaaca aaacaaaaac   1980
agacagaagt cctcactgca cggtgctgga atggatccgg gtcaggaaaa attattacaa   2040
agtgcatgat ggggacattc acaatttgga atatgccttg tacattgtgc aacaaaattc   2100
taccaatgat aaactccaga attttttttg tttttgtttt ttgttttttt aaacgaagtc   2160
tcactctgtt gtccaggctg gagtgcagtg gtgtgatctc agctcattgc aacctctgcc   2220
tcagcctcct gagtagctgg gattacaggc atgagccacc acgcccagcc aattttgta   2280
ttttcggtag agacagcgtt ttaccatcct ggccaggctg gtctcgacct cctgacctcg   2340
aatgatccac ctgcctcggc ctcccaaagt gctgggatta taggcatgag ccaccgcgct   2400
gggtcaaact ccagaattat taaacgactc aatgattgca tcacggttgt gaatggagat   2460
ttttgttca tttgtgatcc atgctgaagg gttagaggt gaagaatcaa tagatttgta   2520
accaaagttg ctctggaaat taaagcaaaa caataaattt agattacata cagagactga   2580
gataaaagca aaggtagcaa atattaacca gttggtgaac ctgggtgaaa actatatact   2640
gttattgcaa cttttctgtg agtttgagat ttttcaaaat gaaaacattg aaaaaaatat   2700
taaaacctca tgaaacttag taaaaattta ttgaatgat                         2739
```

```
<210> SEQ ID NO 10
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 10
tctctcgcct ttccctccct                                                  20

<210> SEQ ID NO 11
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 11
ctcaagcaat ctcccacctc a                                                21

<210> SEQ ID NO 12
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 12
tcccagctac tcaggaggct                                                  20

<210> SEQ ID NO 13
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 13
catgtcttgt gtggctggga t                                                21

<210> SEQ ID NO 14
<211> LENGTH: 22
<212> TYPE: DNA
<213> ORGANISM: Artificial Sequence
<220> FEATURE:
<223> OTHER INFORMATION: Antisense oligonucleotide

<400> SEQUENCE: 14
gagtcatcgg tcctcagagc ag                                               22

<210> SEQ ID NO 15
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 15
attctccttc ctgctaaagc                                                  20

<210> SEQ ID NO 16
<211> LENGTH: 21
<212> TYPE: DNA
<213> ORGANISM: Artificial Sequence
<220> FEATURE:
<223> OTHER INFORMATION: Antisense oligonucleotide
```

<400> SEQUENCE: 16
attatttcgt attgctttgg c                                              21

<210> SEQ ID NO 17
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 17
cacacatgca tacatggact                                                20

<210> SEQ ID NO 18
<211> LENGTH: 22
<212> TYPE: DNA
<213> ORGANISM: Artificial Sequence
<220> FEATURE:
<223> OTHER INFORMATION: Antisense oligonucleotide

<400> SEQUENCE: 18
ctcagttctc tgacgctttg ag                                             22

<210> SEQ ID NO 19
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 19
gccacagtgt gaggaacg                                                  18

<210> SEQ ID NO 20
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 20
gtaataattt ttcctgaccc                                                20

<210> SEQ ID NO 21
<211> LENGTH: 22
<212> TYPE: DNA
<213> ORGANISM: Artificial Sequence
<220> FEATURE:
<223> OTHER INFORMATION: Antisense oligonucleotide

<400> SEQUENCE: 21
agtcgtttaa taattctgga gt                                             22

<210> SEQ ID NO 22
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 22
ttactaagtt tcatgaggtt                                                20

```
<210> SEQ ID NO 23
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 23
atggctcaac tcacatagca                                              20

<210> SEQ ID NO 24
<211> LENGTH: 22
<212> TYPE: DNA
<213> ORGANISM: Artificial Sequence
<220> FEATURE:
<223> OTHER INFORMATION: Antisense oligonucleotide

<400> SEQUENCE: 24
ttatacaatg tttgcttgga tt                                           22

<210> SEQ ID NO 25
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 25
ttgttgcaca atgtacaag                                               19

<210> SEQ ID NO 26
<211> LENGTH: 22
<212> TYPE: DNA
<213> ORGANISM: Artificial Sequence
<220> FEATURE:
<223> OTHER INFORMATION: Antisense oligonucleotide

<400> SEQUENCE: 26
tggttgctct caggaggcgg ct                                           22

<210> SEQ ID NO 27
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 27
attttagttg ttttctctgg                                              20

<210> SEQ ID NO 28
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 28
cacggtgtgg gactggtggt                                              20

<210> SEQ ID NO 29
<211> LENGTH: 399
<212> TYPE: DNA
<213> ORGANISM: Homo sapiens
```

<400> SEQUENCE: 29

```
tggagtttat cattggtaga attttgttgc acaatgtaca aggcatattc caaattgtga    60
atgtccccat catgcacttt gtaataattt ttcctgaccc ggatccattc cagcaccgtg   120
cagtgaggac ttctgtctgt ttttgttttg ttttaccttc ctccagggaa ggtgtacttt   180
tctgtccaca ggtgtcccgg tgagcggctc accttaattc tctcagggct tgaggtgatt   240
taaggctggc ttcagtcccc acaaagacaa ttctgttgct ggtttacctt tgcttttagg   300
ggatagaact ttgggggtcc ccagaaaaaa cccaaaagtc tttaccaggc cccccgcctg   360
agcctcgact tctgtcctgt ggccacagtg tgaggaacg                         399
```

<210> SEQ ID NO 30
<211> LENGTH: 654
<212> TYPE: DNA
<213> ORGANISM: Homo sapiens

<400> SEQUENCE: 30

```
taatgtgcaa atactgtgcc attttatatc aagtacttga gcacctgcaa attttggtat    60
ctgggagggt cctggaacca ataccccgag gataccatgg gacaactgta gtacatgtgt   120
agtccatgta tgcatgtgtg aatccaagca aacattgtat aaaataata atggaaagaa   180
caggcttggt gcggtggctc acacctgcaa tcccagcact ttggaattgc aggccaacac   240
gggaggatca cttgaggcct ggagtttgaa atcggcctgg gagatgtacc aagacccat   300
ctgtacaaaa aaaaaattta gccagatgcg atggtatatg cctgtgaggc ccagctaccc   360
acgaaattga ggtgggagat tgcttgagct taggagttca aggctgagac gggccatgat   420
cacaccacta cattccagcc tggttgacaa aatgagaccc catctctaaa aaagaaaag   480
aaaaaagaa cagtctacta acaaaacgaa aatactggac aataatcctc tctaagttgg   540
gagaaggata attagagtta cagtgttctg ggtctttta ttttggggag aggggttaaa   600
atattgctta acattaggtc ttcttatgtt gaaattgcat taaaagtgat tagc         654
```

<210> SEQ ID NO 31
<211> LENGTH: 271
<212> TYPE: DNA
<213> ORGANISM: Homo sapiens

<400> SEQUENCE: 31

```
tttttttttt ttttttttttt tttttttttt ttttttttttt tttagagagg ggggctcatt    60
ttgtcaacca ggctggaatg gagggggggg atcatggccc gtctcagcct tgaactccta   120
agctcaagca atctcccacc tcaatttcgg gggtagctgg gcctcacagg catataccat   180
cgcatctggc taaattttttt ttttggacag atggggtctt ggtacatctc ccaggccgat   240
ttcaaactcc aggcctcaag ggatcctccc g                                  271
```

<210> SEQ ID NO 32
<211> LENGTH: 469
<212> TYPE: DNA
<213> ORGANISM: Homo sapiens

<400> SEQUENCE: 32

```
gagatggggt tcattttgt caaccaggct ggaatgtagt ggtgtgatca tggcccgtct    60
cagccttgaa ctcctaagct caagcaatct cccacctcaa tttcgtgggt agctgggcct   120
cacaggcata taccatcgca tctggctaaa ttttttttt gtacagatgg ggtcttggta   180
catctcccag gccgatttca aactccaggc ctcaagtgat cctcccgtgt tggcctgcaa   240
```

```
ttccaaagtg ctgggattgc aggtgtgagc caccgcacca agcctggtct ttccattatt      300 attttttatac aatgtttgct tggattcaca catgcataca tggactacac atgtactaca     360
gttgtcccat ggtatcctcg gggtattggt tccaggaccc tcccagatac caaaatttgc     420
aggtgctcaa gtacttgata taaaatggca cagtatttgc acattacct                 469
```

<210> SEQ ID NO 33
<211> LENGTH: 903
<212> TYPE: DNA
<213> ORGANISM: Homo sapiens

<400> SEQUENCE: 33

```
acacctattt accttttaaa tggctaatac cttttaatgc aatttcacat aagaagacct      60
aatgttaagc aatattttaa cccctctccc caaaataaaa agacccagaa cactgtaact     120
ctaattatcc ttctcccaac ttagagagga ttattgtcca gtattttcgt tttgttagta     180
gactgttctt ttttagaga tggggtctca ttttgtcaac caggctggaa tgtagtggtg     240
tgatcatggc ccgtctcagc cttgaactcc taagctcaag caatctccca cctcaatttc     300
gtgggtagct gggcctcaca ggcatatacc atcgcatctg ctaaatttt ttttttttgt     360 acagatgggg tcttggtaca tctcccaggc cgatttcaaa ctccaggcct caagtgatcc     420
tcccgtgttg gcctgcaatt ccaaagtgct gggattgcag gtgtgagcca ccgcaccaag     480
cctgttcttt ccattattat ttttatacaa tgtttgcttg gattcacaca tgcatacatg     540
gactacacat gtactacagt tgtcccatgg tatcctcggg gtattggttc caggaccctc     600
ccagatacca aaatttgcag gtgctcaagt acttgatata aaatggcaca gtatttgcac     660
attacctacg cacatcctac tgtgtagttt aaatcaagat tacttatagt ccctaaaaca     720
atgtaaatgc tctgtaaata gctgttatac tggattgttt aaaatatgta ttatttcgta     780
ttgctttggc tttaaacata ttttcagtct gcttggttga atccatggat ctgaagccca     840
gtgtaggagg gcccagtgtg ctcttctggg gtaattctcc ttcctgctaa agcgcacgct     900
tac                                                                    903
```

<210> SEQ ID NO 34
<211> LENGTH: 921
<212> TYPE: DNA
<213> ORGANISM: Homo sapiens
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t

```
<220> FEATURE:
<221> NAME/KEY: misc_feature
<222> LOCATION: (760)..(760)
<223> OTHER INFORMATION: n is a, c, g, or t
<220> FEATURE:
<221> NAME/KEY: misc_feature
<222> LOCATION: (821)..(821)
<223> OTHER INFORMATION: n is a, c, g, or t
<220> FEATURE:
<221> NAME/KEY: misc_feature
<222> LOCATION: (826)..(826)
<223> OTHER INFORMATION: n is a, c, g, or t

<400> SEQUENCE: 34
ttgnagcctg gngtttgaat cggcctgggn gnagtaccag naccccatct gtacaaaaaa      60
aaaaaattta gccagatgcg atggtatatg cctgtgaggc ccagctaccc acgaaattga     120
ggtgggagat tgcttgagct taggagttca aggctgagac gggccatgat cacaccacta     180
cattccagcc tggttgacaa aatgagaccc catctctaaa aaaagaacag tctactaaca     240
aaacgaaaat actggacaat aatcctctct aagttgggag aaggataatt agagttacag     300
tgttctgggt cttttattt tggggagagg ggttaaaata ttgcttaaca ttaggtcttc      360
ttatgttgaa attgcattaa aagtgattag ccatttaaaa gtgaaatagt gtgtatatat     420
tccaaattag caaggaggaa aaacataata caaaaaaatt cattaagaaa ctaaaaagta     480
agaaagggag ggaaaggcga gagaaaccat gcaagtacga aactgtctcc aggaacagcg     540
gggtaagacc ctcagtccaa cgaccccaga gaaaacaact aaaatgatgg ataactcgct     600
ttaaaaacaa ttcctcaaag cgtcagagaa ctgagaaaaa cagtaagaaa ccaccagtcc     660
cacaccgtgg tgcaggacac agcaatggaa actgaaattg ttcagaccag ccgncttctg     720
agagcaccat cagaactgga gagcgctgca cggaaccgtn cagggcactg ggagctctga     780
ggagcctctg aggcctcggg gctctgcagg acaagccgg nagggngcgg gggcccgctt      840
ttggggcggg gacttcacac ccctgcagcg tatcccagcc acacaagaat ggcgaacgct     900
gctgcgttcg ttcctaaact g                                              921

<210> SEQ ID NO 35
<211> LENGTH: 443
<212> TYPE: DNA
<213> ORGANISM: Homo sapiens

<400> SEQUENCE: 35
ttttttttaa atggctaatc actttttaatg caatttcaac ataagaagac ctaatgttaa     60
gcaatatttt aaccccctctc cccaaaataa aaagacccag aacactgtaa ctctaattat    120
ccttctccca acttagagag gattattgtc cagtattttc gttttgttag tagactgttc    180 ttttttttctt ttcttttttt agagatgggg tctcattttg tcaaccaggc tggaatgtag   240
tggtgtgatc atggcccgtc tcagccttga actcctaagc tcaagcaatc tcccacctca    300
atttcgtggg tagctgggcc tcacaggcat ataccatcgc atctggctaa atttttttt     360 gtacagatgg ggtcttggta catctcccag gccgatttca aactccaggc tcaagtgat    420 cctcccgtgt tggcctgcaa ttc                                            443

<210> SEQ ID NO 36
<211> LENGTH: 440
<212> TYPE: DNA
<213> ORGANISM: Homo sapiens
```

<400> SEQUENCE: 36

```
gtaattgcta atcactttta atgcaattgc aacataagaa gacctaatgt taagcaatat      60
tttaacccct ctccccaaaa taaaaagacc cagaacactg taactctaat tatccttctc     120
ccaacttaga gaggattatt gtccagtatt ttcgttttgt tagtagactg ttcttttttt     180
cttttctttt tttagagatg gggtctcatt ttgtcaacca ggctggaatg tagtggtgtg     240
atcatggccc gtctcagcct tgaactccta agctcaagca atctcccacc tcaatttcgt     300
gggtagctgg gcctcacagg catataccat cgcatctggc taaattttt ttttgtacag      360
atggggtctt ggtacatctc ccaggccgat ttcaaactcc aggcctcaag tgatcctccc     420
gtgttggcct gcaattccaa                                                 440
```

<210> SEQ ID NO 37
<211> LENGTH: 579
<212> TYPE: DNA
<213> ORGANISM: Homo sapiens

<400> SEQUENCE: 37

```
ccctttttt tttttttta gagatggggt ctcattttgt caaccaggct ggaatgtagt       60
ggtgtgatca tggcccgtct cagccttgaa ctcctaagct caagcaatct cccacctcaa     120
tttcgtgggt agctgggcct cacaggcata ccatcgca tctggctaaa ttttttttt       180
gtacagatgg ggtcttggta catctcccag gccgatttca aactccaggc tcaagtgat    240
cctcccgtgt tggcctgcaa ttccaaagtg ctgggattgc aggtgtgagc caccgcacca    300
agcctgttct ttccattatt atttttatac aatgtttgct tggattcaca catgcataca    360
tggactacac atgtactaca gttgtcccat ggtatcctcg gggtattggt tccaggaccc    420
tcccagatac caaaatttgc aggtgctcaa gtacttgata taaaatggca cagtatttgc    480
acattaccta cgcacatcct actgtgtagt ttaaatcaag attacttata gtccctaaaa    540
caatgtaaat gctctgtaaa tagctgttat actgtattg                            579
```

<210> SEQ ID NO 38
<211> LENGTH: 2082
<212> TYPE: DNA
<213> ORGANISM: Homo sapiens

<400> SEQUENCE: 38

```
gggaggggtt gggtggcctc ggggagcctc ggggagccgg gagcacggca gggcttggag      60
ccccgcttcc ttgcgggcct caggggctgc tctgaggacc gatgactcgg aaagcgctca    120
gaagaacgct tcgcccgttg gtgctatgtg agttgagcca ttactgtctt gttttttctct    180
gttttttgtgt gttttttgaga cagagtcttg ctttgtcgcc caggctgagg tgcagtggcg    240
cgatctcagc tcactgcaac ctccatctcc ggggcttcag cgattttctc acccccagcct    300
cctgagtaaa gcgtgcgctt tagcaggaag gagaattacc ccagaagagc acactgggcc    360
ctccttacac ttggcttcag atccatggat tcaaccaagc agactgaaaa tattgtttta    420
aagccaaagc aatacgaaat aatacatatt ttaaaacaat acagtataac agctatttac    480
agagcattta cattgttttta gggactataa gtaatcttga tttaaactac acagtaggat    540
gtgcgtaggt aatgtgcaaa tactgtgcca ttttatatca agtacttgag cacctgcaaa    600
ttttggtatc tgggagggtc ctggaaccaa taccccgagg ataccatggg acaactgtag    660
tacatgtgta gtccatgtat gcatgtgtga atccaagcaa acattgtata aaaataataa    720
```

```
tggaaagaac aggcttggtg cggtggctca cacctgcaat cccagcactt tggaattgca    780
ggccaacacg ggaggatcac ttgaggcctg gagtttgaaa tcggcctggg agatgtacca    840
agaccccatc tgtacaaaaa aaaaatttag ccagatgcga tggtatatgc ctgtgaggcc    900
cagctaccca cgaaattgag gtgggagatt gcttgagctt aggagttcaa ggctgagacg    960
ggccatgatc acaccactac attccagcct ggttgacaaa atgagacccc atctctaaaa   1020
aaagaaaaga aaaaagaac agtctactaa caaaacgaaa atactggaca ataatcctct    1080
ctaagttggg agaaggataa ttagagttac agtgttctgg gtctttttat tttggggaga   1140
ggggttaaaa tattgcttaa cattaggtct tcttatgttg aaattgcatt aaaagtgatt   1200
agccatttaa aagtgaaata gtgtgtatat attccaaatt agcaaggagg aaaaacataa   1260
tacaaaaaaa ttcattaaga aactaaaaag taagaaaggg agggaaaggc gagagaaacc   1320
atgcaagtac agaactgtct ccaggaacag cggggtaaga ccctcagtcc aacgacccca   1380
gagaaaacaa ctaaaatgat ggataactcg ctttaaaaac aattcctcaa agcgtcagag   1440
aactgagaaa aacagtaaga aaccaccagt cccacaccgt ggtgcaggac acagcaatgg   1500
aaactgaatt gtttcagacc agccgcctcc tgagagcaac catcagaact ggagagcgct   1560
gaacggaacc gtccagggca ctgggagctc tgaggagcct ctgaggcctc ggggctctgc   1620
agggacaagc cgggaggggg cggggcccgc tttgggcgg cgactccaca cccctgcagc   1680
gtatcccagc cacacaagac atggcgcaca gctgctgcgt cgttcctca cactgtggcc   1740 acaggacaga agtcgaggct caggcggggg gcctggtaaa gactttgggt ttttcttggg   1800
accccaaagt tctatcccct aaaagcaaag gtaaaccagc aacagaattg tctttgtggg   1860
gactgaagcc agccttaaat cacctcaagc cctgagagaa ttaaggtgag ccgctcaccg   1920
ggacacctgt ggacagaaaa gtacaccttc cctggaggaa ggtaaaacaa acaaaaaaca   1980
gacagaagtc ctcactgcac ggtgctggaa tggatccggg tcaggaaaaa ttattacaaa   2040
gtgcatgatg gggacattca caatttggaa tatgccttgt ac                      2082
```

<210> SEQ ID NO 39
<211> LENGTH: 501
<212> TYPE: DNA
<213> ORGANISM: Homo sapiens
<220> FEATURE:
<221> NAME/KEY: misc_feature
<222> LOCATION: (448)..(448)
<223> OTHER INFORMATION: n is a, c, g, or t
<220> FEATURE:
<221> NAME/KEY: misc_feature
<222> LOCATION: (484)..(484)
<223> OTHER INFORMATION: n is a, c, g, or t

<400> SEQUENCE: 39

```
atcattcaat aaattttac taagtttcat gaggttttaa tatttttttc aatgttttca     60
ttttgaaaaa tctcaaactc acagaaaagt tgcaataaca gtatatagtt ttcacccagg   120
ttcaccaacc tgttaatatt ttgctacctt tgctttatc tcagtctctg tatgtaatct    180
aaatttattg tttgcttta atttccagag caactttggt tacaaatcta ttgattcttc    240
acctctaaac ccttcagcat ggatcacaaa tgaacaaaaa atctccattc acaaccgtga   300
tgcaatcatt gagtcgttta ataattctgg agtttgaccc agcgcggtgg ctcatgccta   360
taatcccagc actttgggag gccgaggcag gtggatcatt cgaggcagg agggcgagac   420 cagcctggcc aggatggtaa aacgctgnct ctaccgaaaa tacaaaaatt ggcctgggcg   480
tggngggctc atgcctgtta t                                             501
```

<210> SEQ ID NO 40
<211> LENGTH: 240
<212> TYPE: DNA
<213> ORGANISM: Homo sapiens
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (238)..(238)
<223> OTHER INFORMATION: n is a, c, g, or t

<400> SEQUENCE: 40
tgagacagag acttgctttg tcgcccaggc tgaggtggca gnggcgcgat ctcagctcac    60
tgcaacctcc atctccgggg ctccagcgat tttctcaccc cagcctcctn aggaaagcgt   120
gcgctttagc aggaaggaga attaccccag aagagcacac tgggccctcc ttacacttgg   180
cttcagatcc atggnttcaa ccaagcagan tgaaaatatg gttttaaagc caaagcanta   240

<210> SEQ ID NO 41
<211> LENGTH: 417
<212> TYPE: DNA
<213> ORGANISM: Homo sapiens
<220> FEATURE:
<221> NAME/KEY: misc_feature
<222> LOCATION: (321)..(321)
<223> OTHER INFORMATION: n is a, c, g, or t

<400> SEQUENCE: 41
aaatggctaa tcacttttaa tgcaatttca acataagaag acctaatgtt aagcaatatt    60
ttaacccctc tccccaaaat aaaaagaccc agaacactgt aactctaatt atccttctcc   120
caacttagag aggattattc gtccagtatt ttcgttttgt tagtagactg ttcttttttt   180
cttttctttt tttagagatg gggtctcatt ttgtcaacca ggctgaaatg tagtggtgtg   240
atcatggccc gtctcagcct tgaactccta agctcaagca atctcccacc tcaatttcgt   300
gggtagctgg gcctcacagg nattatacca tcgcatctgg ctaaattttt tttttgtaca   360
gatggggtct tggtacatct cccaggccga tttcaaactc caggcctcaa gtgatcc     417

<210> SEQ ID NO 42
<211> LENGTH: 427
<212> TYPE: DNA
<213> ORGANISM: Homo sapiens

<400> SEQUENCE: 42
taatgtgcaa atactgtgcc attttatatc aagtacttga gcacctgcaa attttggtat    60
ctgggagggt cctggaacca ataccccgag gataccatgg gacaactgta gtacatgtgt   120
agtccatgta tgcatgtgtg aatccaagca acattgtat aaaaataata atggaaagaa   180
caggcttggt gcgtggctc acacctgcaa tcccagcact ttggaattgc aggccaacac   240
gggaggatca cttgaggcct ggagtttgaa atcggcctgg gagatgtacc aagaccccat   300

```
ctgtacaaaa aaaaaattta gccagatgcc gatgggtata tgcctgtgag gcccagctac    360
ccacgaaatt gaggtgggag attgcttgag cttaggagtt caaggctgag acgggccatg    420
atcacac                                                              427
```

```
<210> SEQ ID NO 43
<211> LENGTH: 398
<212> TYPE: DNA
<213> ORGANISM: Homo sapiens
<220> FEATURE:
<221> NAME/KEY: misc_feature
<222> LOCATION: (313)..(313)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t

<400> SEQUENCE: 43
```

```
gtaatgtgca aatactgtgc cattttatat caagtacttg agcacctgca aattttggta     60
tctgggaggg tcctggaacc aatacccga ggataccatg gacaactgt agtacatgtg     120 tagtccatgt atgcatgtgt gaatccaagc aaacattgta taaaaataat aatggaaaga   180
acaggcttgg tgcggtggct cacacctgca atcccagcac tttggaattg caggccaaca   240
cgggaggatc acttgaggcc tgggagtttg aaatcggcct ggggagatgt accaagaccc    300
cattctgtta cananaaaaa tttaggccag atggcgatgg tattttgcct gtggaggccc    360
cagcttaccc cacggaattt gaggtggggg nggtttgt                            398
```

```
<210> SEQ ID NO 44
<211> LENGTH: 470
<212> TYPE: DNA
<213> ORGANISM: Homo sapiens

<400> SEQUENCE: 44
```

```
ggaattaaag gttttgggga cttgagatgt tttgtttgag ctaattactg aatgatgccc     60
tgcctgagac agagacagag acagagagag agagagagaa agagagagag agagagagaa    120
catatgagaa cacagagaaa acaactaaaa tgatggataa ctcgctttaa aaacaattcc    180
tcaaagcgtc agagaactga gaaaaacagt aagaaaccac cagtcccaca ccgtggtgca    240
ggacacagca atggaaactg aattgtttca gaccagccgc ctcctgagag caaccatcag    300
aactggagag cgctgcacgg aaccgtccag ggcactggga gctctgagga gcctctgagg    360
cctcggggct ctgcagggac aagccgggag agggcgggc gctattgggg cggcgactcc    420 acaccctgc agcgtatccc agccacacaa gacatggcga cacgctgctg             470
```

```
<210> SEQ ID NO 45
<211> LENGTH: 375
<212> TYPE: DNA
<213> ORGANISM: Homo sapiens
<220> FEATURE:
<221> NAME/KEY: misc_feature
<222> LOCATION: (214)..(214)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
```

```
<220> FEATURE:
<221> NAME/KEY: misc_feature
<222> LOCATION: (332)..(332)
<223> OTHER INFORMATION: n is a, c, g, or t

<400> SEQUENCE: 45
tggagtttat cattggtaga attttgttgc acaatgtaca aggcatattc caaattgtga      60
atgtccccat catgcacttt gtaataattt ttcctgaccc ggatccattc cagcaccgtg     120
cagtgaggac ttctgtctgt ttttgttttg ttttaccttc ctccagggga aggtgtactt     180
ttctgtccac aggtgtcccg gtgaggcggc tcancttaat tctctcaggg cttgagggtg     240
atttaaggct gggctttcag tccccacaaa gacaattctg ttgctgggtt acctttgctt     300 taggggggata gaactttngg ggtaccaagg anaaacccca agtctttaca gggggccccc     360
cgcctgaggg cctcg                                                       375
```

TREATMENT OF ALPHA-L-IDURONIDASE (IDUA) RELATED DISEASES BY INHIBITION OF NATURAL ANTISENSE TRANSCRIPT TO IDUA

This application is a Divisional of U.S. patent application Ser. No. 14/925,196 filed Oct. 28, 2015, which is a Divisional of U.S. patent application Ser. No. 13/880,409 filed Apr. 19, 2013, now U.S. Pat. No. 9,222,088, which is a National Phase Application of PCT/US2011/057097 filed Oct. 20, 2011, which claims benefit to U.S. Provisional Patent Application No. 61/405,758 filed Oct. 22, 2010, which are all incorporated herein by reference in their entirety.

FIELD OF THE INVENTION

Embodiments of the invention comprise oligonucleotides modulating expression and/or function of IDUA and associated molecules.

BACKGROUND

DNA-RNA and RNA-RNA hybridization are important to many aspects of nucleic acid function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H, an activity that is present in most cell types. Antisense molecules can be delivered into cells, as is the case for oligodeoxynucleotides (ODNs), or they can be expressed from endogenous genes as RNA molecules. The FDA recently approved an antisense drug, VITRAVENE™ (for treatment of cytonegalovirus retinitis), reflecting that antisense has therapeutic utility.

SUMMARY

This Summary is provided to present a summary of the invention to briefly indicate the nature and substance of the invention. It is submitted with the understanding that it will not be used to interpret or limit the scope or meaning of the claims.

In one embodiment, the invention provides methods for inhibiting the action of a natural antisense transcript by using antisense oligonucleotide(s) targeted to any region of the natural antisense transcript resulting in up-regulation of the corresponding sense gene. It is also contemplated herein that inhibition of the natural antisense transcript can be achieved by siRNA, ribozymes and small molecules, which are considered to be within the scope of the present invention.

One embodiment provides a method of modulating function and/or expression of an IDUA polynucleotide in biological systems, including, but not limited to, patient cells or tissues in vivo or in vitro comprising contacting said biological system or said cells or tissues with an antisense oligonucleotide of about 5 to about 30 nucleotides in length wherein said oligonucleotide has at least 50% sequence identity to a reverse complement of a polynucleotide comprising 5 to 30 consecutive nucleotides within nucleotides 1 to 2695 of SEQ ID NO: 2 or 1 to 2082 of SEQ ID NO: 3 or 1 to 322 of SEQ ID NO: 4 or 1 to 677 of SEQ ID NO: 5 or 1 to 716 of SEQ ID NO: 6 or 1 to 466 of SEQ ID NO: 7 or 1 to 1255 of SEQ ID NO: 8 or 1 to 2739 of SEQ ID NO: 9 thereby modulating function and/or expression of the IDUA polynucleotide in said biological system including said patient cells or tissues in vivo or in vitro.

In an embodiment, an oligonucleotide targets a natural antisense sequence of IDUA polynucleotides present in a biological system, for example, nucleotides set forth in SEQ ID NOS: 2 to 9, and any variants, alleles, homologs, mutants, derivatives, fragments and complementary sequences thereto. Examples of antisense oligonucleotides are set forth as SEQ ID NOS: 10 to 28.

Another embodiment provides a method of modulating function and/or expression of an IDUA polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of an antisense of the IDUA polynucleotide; thereby modulating function and/or expression of the IDUA polynucleotide in patient cells or tissues in vivo or in vitro.

Another embodiment provides a method of modulating function and/or expression of an IDUA polynucleotide in patient cells or tissues in vivo or in vitro comprising contacting said cells or tissues with an antisense oligonucleotide 5 to 30 nucleotides in length wherein said oligonucleotide has at least 50% sequence identity to an antisense oligonucleotide to an IDUA polynucleotide; thereby modulating function and/or expression of the IDUA polynucleotide in patient cells or tissues in vivo or in vitro.

In another embodiment, the invention comprises a method of modulating the function or expression of an IDUA polynucleotide in a biological system comprising contacting said biological system with at least one antisense oligonucleotide that targets a natural antisense transcript of the IDUA polynucleotide thereby modulating the function and/or expression of the IDUA polynucleotide in said biological system.

In another embodiment, the invention comprises a method of modulating the function or expression of an IDUA polynucleotide in a biological system comprising contacting said biological system with at least one antisense oligonucleotide that targets a region of a natural antisense transcript of the IDUA polynucleotide thereby modulating the function and/or expression of the IDUA polynucleotide in said biological system.

In an embodiment, the invention comprises a method of increasing the function and/or expression of an IDUA polynucleotide having SEQ ID NO. 1 in a biological system comprising contacting said biological system with at least one antisense oligonucleotide that targets a natural antisense transcript of said IDUA polynucleotide thereby increasing the function and/or expression of said IDUA polynucleotide or expression product thereof.

In another embodiment, the invention comprises a method of increasing the function and/or expression of an IDUA polynucleotide having SEQ ID NO. 1 in a biological system comprising contacting said biological system with at least one antisense oligonucleotide that targets a natural antisense transcript of said IDUA polynucleotide thereby increasing the function and/or expression of said IDUA polynucleotide or expression product thereof wherein the natural antisense transcripts are selected from SEQ ID NOS. 2 to 9.

In another embodiment, the invention comprises a method of method of increasing the function and/or expression of an IDUA polynucleotide having SEQ ID NO. 1 in a biological system comprising contacting said biological system with at least one antisense oligonucleotide that targets a natural antisense transcript of said IDUA polynucleotide thereby increasing the function and/or expression of said IDUA polynucleotide or expression product thereof wherein the natural antisense transcripts are selected from SEQ ID NOS. 2 to 9 and wherein the antisense oligonucleotides are selected from at least one of SEQ ID NOS. 10 to 28.

In an embodiment, a composition comprises one or more antisense oligonucleotides which bind to sense and/or antisense IDUA polynucleotides.

In an embodiment, the oligonucleotides comprise one or more modified or substituted nucleotides.

In an embodiment, the oligonucleotides comprise one or more modified bonds.

In yet another embodiment, the modified nucleotides comprise modified bases comprising phosphorothioate, methylphosphonate, peptide nucleic acids, 2'-O-methyl, fluoro- or carbon, methylene or other locked nucleic acid (LNA) molecules. Preferably, the modified nucleotides are locked nucleic acid molecules, including α-L-LNA.

In an embodiment, the oligonuclotides are administered to a patient by any delivery route including, but not limited to, orally, transdermally, via inhalation means, subcutaneously, intramuscularly, intravenously or intraperitoneally.

In an embodiment, the oligonucleotides are administered in a pharmaceutical composition. A treatment regimen comprises administering the antisense compounds at least once to patient; however, this treatment can be modified to include multiple doses over a period of time. The treatment can be combined with one or more other types of therapies.

In an embodiment, the oligonucleotides are encapsulated in a liposome or attached to a carrier molecule (e.g. cholesterol. TAT peptide).

Other aspects are described infra.

Figure 1:
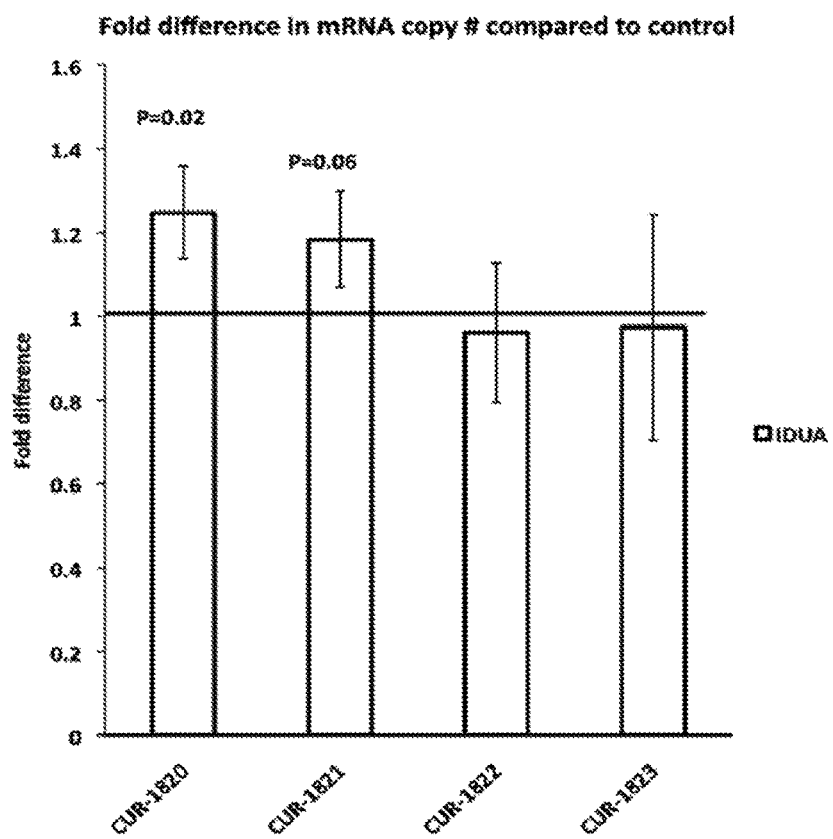
FIG. 1 is a graph of real time PCR results showing the fold change+standard deviation in IDUA mRNA after treatment of HepG2 cells with phosphorothioate oligonucleotides introduced using Lipofectamine 2000, as compared to control. Bars denoted as CUR-1820 to CUR-1823 correspond to samples treated with SEQ ID NOS: 10 to 13 respectively.

Sequence Listing Description—SEQ ID NO: 1: *Homo sapiens* iduronidase, alpha-L-(IDUA), mRNA (NCBI Accession No.: NM_000203); SEQ ID NO: 2: Natural IDUA antisense sequence (HS.656285); SEQ ID NO: 3: Natural IDUA antisense sequence (CR626108); SEQ ID NO: 4: Natural IDUA antisense sequence (DN334757); SEQ ID NO: 5: Natural IDUA antisense sequence (DN876121); SEQ ID NO: 6: Natural IDUA antisense sequence (DN744190); SEQ ID NO: 7: Natural IDUA antisense sequence (DN330918); SEQ ID NO: 8: Natural IDUA antisense sequence (DN876121-extended); SEQ ID NO: 9: human IDUA natural antisense-extended; SEQ ID NOs: 10 to 28: Antisense oligonucleotides. * indicates phosphothioate bond; SEQ ID NOs: 29 to 45: UniGene Cluster Hs.656285.

DETAILED DESCRIPTION

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians reptiles, and birds. In an embodiment, the genes or nucleic acid sequences are human.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "mRNA" means the presently known mRNA transcript(s) of a targeted gene, and any further transcripts which may be elucidated.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA. An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

In the context of this invention, the term "oligonucleotide" refers to an oligomer or polymer of ribonucleic acid (RNA) or deoxyribonucleic acid (DNA) or mimetics thereof. The term "oligonucleotide", also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoögsteen or reverse Hoögsteen types of base pairing, or the like.

The oligonucleotide may be "chimeric", that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide in the case of an oligonucleotides compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleosides and/or oligonucleotide analogs as described above.

The oligonucleotide can be composed of regions that can be linked in "register", that is, when the monomers are linked consecutively, as in native DNA, or linked via spacers. The spacers are intended to constitute a covalent "bridge" between the regions and have in preferred cases a length not exceeding about 100 carbon atoms. The spacers may carry different functionalities, for example, having positive or negative charge, carry special nucleic acid binding properties (intercalators, groove binders, toxins, fluorophors etc.), being lipophilic, inducing special secondary structures like, for example, alanine containing peptides that induce alpha-helices.

As used herein "IDUA" and "Alpha-L-Iduronidase" are inclusive of all family members, mutants, alleles, fragments, species, coding and noncoding sequences, sense and antisense polynucleotide strands, etc.

As used herein, the words 'Alpha-L-iduronidase', IDA, IDUA and MPS1, are considered the same in the literature and are used interchangeably in the present application.

As used herein, the term "oligonucleotide specific for" or "oligonucleotide which targets" refers to an oligonucleotide having a sequence (i) capable of forming a stable complex with a portion of the targeted gene, or (ii) capable of forming a stable duplex with a portion of a mRNA transcript of the targeted gene. Stability of the complexes and duplexes can be determined by theoretical calculations and/or in vitro assays. Exemplary assays for determining stability of hybridization complexes and duplexes are described in the Examples below.

As used herein, the term "target nucleic acid" encompasses DNA, RNA (comprising premRNA and mRNA) transcribed from such DNA, and also cDNA derived from such RNA, coding, noncoding sequences, sense or antisense polynucleotides. The specific hybridization of an oligomeric compound with its target nucleic acid interferes with the normal function of the nucleic acid. This modulation of function of a target nucleic acid by compounds, which specifically hybridize to it, is generally referred to as "antisense". The functions of DNA to be interfered include, for example, replication and transcription. The functions of RNA to be interfered, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

RNA interference "RNAi" is mediated by double stranded RNA (dsRNA) molecules that have sequence-specific homology to their "target" nucleic acid sequences. In certain embodiments of the present invention, the mediators are 5-25 nucleotide "small interfering" RNA duplexes (siRNAs). The siRNAs are derived from the processing of dsRNA by an RNase enzyme known as Dicer. siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion. Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non limiting embodiments, siRNAs can comprise about 5 to about 40 nt, about 5 to about 30 nt, about 10 to about 30 nt, about 15 to about 25 nt, or about 20-25 nucleotides.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

By "enzymatic RNA" is meant an RNA molecule with enzymatic activity (Cech, (1988) *J. American. Mad. Assoc.* 260, 3030-3035). Enzymatic nucleic acids (ribozymes) act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through base pairing, and once bound to the correct site, acts enzymatically to cut the target RNA.

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA. This is meant to be a specific example. Those in the art will recognize that this is but one example, and other embodiments can be readily generated using techniques generally known in the art.

As used herein, the term "monomers" typically indicates monomers linked by phosphodiester bonds or analogs thereof to form oligonucleotides ranging in size from a few monomeric units, e.g., from about 3-4, to about several hundreds of monomeric units. Analogs of phosphodiester linkages include: phosphorothioate, phosphorodithioate, methylphosphonates, phosphoroselenoate, phosphoramidate, and the like, as more fully described below.

The term "nucleotide" covers naturally occurring nucleotides as well as nonnaturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleotides described in Benner e al., U.S. Pat. No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and 2'-hydroxyl sugars, e.g., as described in Kornberg and Baker, DNA Replication, 2nd Ed. (Freeman, San Francisco, 1992) as well as their analogs.

"Analogs" in reference to nucleotides includes synthetic nucleotides having modified base moieties and/or modified sugar moieties (see e.g., described generally by Scheit, Nucleotide Analogs, John Wiley, New York, 1980; Freier & Altmann, (1997) *Nucl. Acid. Res.*, 25(22), 4429-4443, Toulmé, J J., (2001) *Nature* Biotechnology 19:17-18; Manoharan M., (1999) *Biochemica et Biophysica Acta* 1489:117-139; Freier S. M., (1997) *Nucleic Acid Research*, 25:4429-4443, Uhlman, E., (2000) *Drug Discovery & Development*, 3: 203-213, Herdewin P., (2000) *Antisense & Nucleic Acid Drug Dev.*, 10:297-310); 2'4), 3'-C-linked [3.2.0] bicycloarabinonucleosides. Such analogs include synthetic nucleotides designed to enhance binding properties, e.g., duplex or triplex stability, specificity, or the like.

As used herein, "hybridization" means the pairing of substantially complementary strands of oligomeric compounds. One mechanism of pairing involves hydrogen bonding, which may be Watson-Crick, Hoögsteen or reversed Hoögsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. In general, stringent hybridization conditions comprise low concentrations (<0.15M) of salts with inorganic cations such as Na+ or K+(i.e., low ionic strength), temperature higher than 20° C.-25° C. below the Tm of the oligomeric compound:target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1× sodium chloride-sodium citrate buffer (SSC)/0.1% (w/v) SOS at 60° C. for 30 minutes.

"Complementary," as used herein, refers to the capacity for precise pairing between two nucleotides on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between the oligonuclotides and the target nucleic acid is considered to be a complementary position. The oligomeric compound and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which are used to indicate a sufficient degree of precise pairing or complementarity over a sufficient number of nucleotides such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining non-complementary nucleotides may be clustered or interspersed with complementary nucleotides and need not be contiguous to each other or to complementary nucleotides. As such, an antisense compound which is 18 nucleotides in length having 4 (four) non-complementary nucleotides which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art. Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.*, (1981) 2, 482-489).

As used herein, the term "Thermal Melting Point (Tm)" refers to the temperature, under defined ionic strength, pH, and nucleic acid concentration, at which 50% of the oligonucleotides complementary to the target sequence hybridize to the target sequence at equilibrium. Typically, stringent conditions will be those in which the salt concentration is at least about 0.01 to 1.0 M Na ion concentration (or other salts) at pH 7.0 to 83 and the temperature is at least about 30° C. for short oligonucleotides (e.g., 10 to 50 nucleotide). Stringent conditions may also be achieved with the addition of destabilizing agents such as formamide.

As used herein, "modulation" means either an increase (stimulation) or a decrease (inhibition) in the expression of a gene.

The term "variant", when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radioisotope, fluorescent, and enzyme label.

As used herein, the term "animal" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

As used herein a "Neurological disease or disorder" refers to any disease or disorder of the nervous system and/or visual system. "Neurological disease or disorder" include disease or disorders that involve the central nervous system (brain, brainstem and cerebellum), the peripheral nervous system (including cranial nerves), and the autonomic nervous system (parts of which are located in both central and peripheral nervous system). A Neurological disease or disorder includes but is not limited to acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Alzheimer's disease; Vascular dementia; amyotrophic lateral sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia telegiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Maric-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; DandyWalker syndrome; Dawson disease; De Morsier's syndrome; Dejcrine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahs syndrome; fainting; familial spastic paralysis; febrile seizures; Fisher syndrome; Friedreich's ataxia; fronto-temporal dementia and other "tauopathics"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactic a polyneuritiformis; herpes zoster oticus; herpes zoster; Hirayama syndrome; HIVassociated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Keams-Sayre syndrome; Kennedy disease Kinsboume syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme disease-neurological sequelae; Machado-Joseph disease; macrencephaly; megalenecphaly: Melkersson-Rosenthal syndrome; Menieres disease; meningitis; Menkes disease; metachromatic leukodystrophy; microcephaly; migraine; Miller Fisher syndrome; mini-strokes; mitochondrial myopathics; Mobius syndrome; monomelic amyotrophy; motor neuron disease; Moyamoya disease; mucopolysaccharidoses; milti-infarct dementia; multifocal motor neuropathy; multiple sclerosis and other demyelinating disorders; multiple system atrophy with postural hypotension; muscular dystrophy; myasthenia gravis; myelinoelastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuseinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis: orthostatic hypotension; overuse syndrome; paresthesia; a neurodegenerative disease or disorder (Parkinson's disease, Huntington's disease, Alzheimer's disease, amyotrophic lateral sclerosis (ALS), dementia, multiple sclerosis and other diseases and disorders associated with neuronal cell death); paramyotonia congenital; parancoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocalleukoencephalopathy; progressive sclerosing poliodystrophy; progressive supranuclear palsy; pseudotumor cerebri; Ramsay-Hunt syndrome (types 1 and 11); Rasmussen's encephalitis; reflex sympathetic dystrophy syndrome; Refsum disease; repetitive motion disorders; repetitive stress injuries; restless legs syndrome; retrovirus-associated myclopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute selerosing panencephalitis; subcortical arteriosclerotic encephalopathy; Sydenham chorea; syncope; syringomyelia; tardive dyskinesia; Tay-Sachs disease; temporal arteritis: tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome; Wildon's disease; and Zellweger syndrome.

Polynucleoside and Oligonucleotide Compositions and Molecules

Targets:

In one embodiment, the targets comprise nucleic acid sequences of Alpha-L-Iduronidase (IDUA), including without limitation sense and/or antisense noncoding and/or coding sequences associated with IDUA.

Alpha-L-Iduronidase (a-L-Iduronidase or a-L-iduronide iduronohydrolase E.C.3.2.1.76; IDUA) is a lysosomal hydrolase required for the breakdown of the glycosaminoglycans heparin sulfate and dermatan sulfate. Lysosomal enzymes undergo a series of processing and maturation events for which IDUA has served as a model.

The lysosomal hydrolase a-L-iduronidase (IDUA) is one of the enzymes in the metabolic pathway responsible for the degradation of the glycosaminoglycans heparan sulfate and dermatan sulfate. In humans a deficiency of IDUA leads to the accumulation of glycosaminoglycans, resulting in the lysosomal storage disorder mucopolysaccharidosis type 1.

A genetic deficiency of the carbohydrate-cleaving, lysosomal enzyme .alpha.-L-iduronidase causes a lysosomal storage disorder known as mucopolysaccharidosis I (MPS I). In a severe form, MPS I is commonly known as Hurler syndrome and is associated with multiple problems such as mental retardation, clouding of the cornea, coarsened facial features, cardiac disease, respiratory disease, liver and spleen enlargement, hernias, and joint stiffness. Patients suffering from Hurler syndrome usually die before age 10. In an intermediate form known as Hurler-Scheie syndrome, mental function is generally not severely affected, but physical problems may lead to death by the teens or twenties. Scheie syndrome is the mildest form of MPS 1. It is compatible with a normal life span, but joint stiffness, corneal clouding and heart valve disease cause significant problems.

Type I mucopolysacchandosis (MPS), also known as Hurler's syndrome, is an inherited metabolic disease caused by a defect in the enzyme .alpha.-L-iduronidase (IDUA), which functions to degrade mucopolysaccharides. An insufficient level of IDUA causes a pathological buildup of heparan sulfate and dermatan sulfate in, e.g., the heart, liver, and central nervous system. Symptoms including neurodegeneration and mental retardation appear during childhood and early death can occur due to organ damage. Typically, treatment includes intravenous enzyme replacement therapy with recombinant IDUA. However, systemically administered recombinant IDUA does not cross the blood brain barrier (BBB), and therefore has little impact on the effects of the disease in the central nervous system (CNS).

In an embodiment, antisense oligonucleotides are used to prevent or treat diseases or disorders associated with IDUA family members. Exemplary Alpha-L-Iduronidase (IDUA) mediated diseases and disorders which can be treated with the antisensense oligonucleotides of the invention and/or with cell/tissues regenerated from stem cells obtained using and/or having the antisense compounds comprise: a disease or disorder associated with abnormal function and/or expression of Alpha-L-Iduronidase; Mucopolysaccharidosis I (MPS 1); a disease or disorder associated with abnormal levels of of heparan sulfate and/or dermatan sulfate; a neurological disease or disorder, a neurodegenerative disease or disorder, long-term memory impairment, Hurler syndrome; Hurler-Scheie syndrome and Scheie syndrome etc.

In an embodiment, modulation of IDUA by one or more antisense oligonucleotides is administered to a patient in need thereof, to prevent or treat any disease or disorder related to IDUA abnormal expression, function, activity as compared to a normal control.

In an embodiment, the oligonucleotides are specific for polynucleotides of IDUA, which includes, without limitation noncoding regions. The IDUA targets comprise variants of IDUA; mutants of IDUA, including SNPs; noncoding sequences of IDUA; alleles, fragments and the like. Preferably the oligonucleotide is an antisense RNA molecule.

In accordance with embodiments of the invention, the target nucleic acid molecule is not limited to IDUA polynucleotides alone but extends to any of the isoforms, receptors, homologs non-coding regions and the like of IDUA.

In an embodiment, an oligonucleotide targets a natural antisense sequence (natural antisense to the coding and non-coding regions) of IDUA targets, including, without limitation, variants, alleles, homologs, mutants, derivatives, fragments and complementary sequences thereto. Preferably the oligonucleotide is an antisense RNA or DNA molecule.

In an embodiment, the oligomeric compounds of the present invention also include variants in which a different base is present at one or more of the nucleotide positions in the compound. For example, if the first nucleotide is an adenine, variants may be produced which contain thymidine, guanosine, cytidine or other natural or unnatural nucleotides at this position. This may be done at any of the positions of the antisense compound. These compounds are then tested using the methods described herein to determine their ability to inhibit expression of a target nucleic acid.

In some embodiments, homology, sequence identity or complementarity, between the antisense compound and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97% about 98%, about 99% or about 100%.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired. Such conditions include, i.e., physiological conditions in the case of in vivo assays or therapeutic treatment, and conditions in which assays are performed in the case of in vitro assays.

An antisense compound, whether DNA, RNA, chimeric, substituted etc, is specifically hybridizable when binding of the compound to the target DNA or RNA molecule interferes with the normal function of the target DNA or RNA to cause a loss of utility, and there is a sufficient degree of complementarily to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

In an embodiment, targeting of IDUA including without limitation, antisense sequences which are identified and expanded, using for example, PCR, hybridization etc., one or more of the sequences set forth as SEQ ID NOS: 2 to 9, and the like, modulate the expression or function of IDUA. In one embodiment, expression or function is up-regulated as compared to a control. In an embodiment, expression or function is down-regulated as compared to a control.

In an embodiment, oligonucleotides comprise nucleic acid sequences set forth as SEQ ID NOS: 10 to 28 including antisense sequences which are identified and expanded, using for example, PCR, hybridization etc. These oligonucleotides can comprise one or more modified nucleotides, shorter or longer fragments, modified bonds and the like. Examples of modified bonds or internucleotide linkages comprise phosphorothioate, phosphorodithioate or the like. In an embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In embodiments of the present invention oligomeric antisense compounds, particularly oligonucleotides, bind to target nucleic acid molecules and modulate the expression and/or function of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The antisense compounds, include, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes Alpha-L-Iduronidase (IDUA).

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

In an embodiment, the antisense oligonucleotides bind to the natural antisense sequences of Alpha-L-Iduronidase (IDUA) and modulate the expression and/or function of IDUA (SEQ ID NO: 1). Examples of antisense sequences include SEQ ID NOS: 2 to 28.

In an embodiment, the antisense oligonucleotides bind to one or more segments of Alpha-L-Iduronidase (IDUA) polynucleotides and modulate the expression and/or function of IDUA. The segments comprise at least five consecutive nucleotides of the IDUA sense or antisense polynucleotides.

In an embodiment, the antisense oligonucleotides are specific for natural antisense sequences of IDUA wherein binding of the oligonucleotides to the natural antisense sequences of IDUA modulate expression and/or function of IDUA.

In an embodiment, oligonucleotide compounds comprise sequences set forth as SEQ ID NOS: 10 to 28, antisense sequences which are identified and expanded, using for example, PCR, hybridization etc These oligonucleotides can comprise one or more modified nucleotides, shorter or longer fragments, modified bonds and the like. Examples of modified bonds or internucleotide linkages comprise phosphorothioate, phosphorodithioate or the like. In an embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate alkylphosphate, alkanephosphate, phosphorothioate and the like. The preparation of the above-noted phosphate analogs, and their incorporation into nucleotides, modified nucleotides and oligonucleotides, per se, is also known and need not be described here.

Since, as is known in the art, the translation initiation codon is typically 5'-AUG (i transcribed mRNA molecules: 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG; and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding Alpha-L-Iduronidase (IDUA), regardless of the sequence(s) of such codons. A translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3) from a translation termination codon. Consequently, the "start codon region" (or "translation initiation codon region") and the "stop codon region" (or "translation termination codon region") are all regions that may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a targeted region is the intragenic region encompassing the translation initiation or termination codon of the open reading frame (ORF) of a gene.

Another target region includes the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene). Still another target region includes the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-S' triphosphate linkage. The 5' cap region of an mRNA is considered to include the 5' cap structure itself as well as the first 50 nucleotides adjacent to the cap site. Another target region for this invention is the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. In one embodiment, targeting splice sites, i.e., intron-exon junctions or exon-intron junctions, is particularly useful in situations where aberrant splicing is implicated in disease, or where an overproduction of a particular splice product is implicated in disease. An aberrant fusion junction due to rearrangement or deletion is another embodiment of a target site. mRNA transcripts produced via the process of splicing of two (or more) mRNAs from different gene sources are known as "fusion transcripts". Introns can be effectively targeted using antisense compounds targeted to, for example, DNA or pre-mRNA.

In an embodiment, the antisense oligonucleotides bind to coding and/or non-coding regions of a target polynucleotide and modulate the expression and/or function of the target molecule.

In an embodiment, the antisense oligonucleotides bind to natural antisense polynucleotides and modulate the expression and/or function of the target molecule.

In an embodiment, the antisense oligonucleotides bind to sense polynucleotides and modulate the expression and/or function of the target molecule.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also embodiments of target nucleic acids.

The locations on the target nucleic acid to which the antisense compounds hybridize are defined as at least a 5-nucleotide long portion of a target region to which an active antisense compound is targeted.

While the specific sequences of certain exemplary target segments are set firth herein, one of skill in the art will recognize that these serve to illustrate and describe particular embodiments within the scope of the present invention. Additional target segments are readily identifiable by one having ordinary skill in the art in view of this disclosure.

Target segments 5-100 nucleotides in length comprising a stretch of at least five (5) consecutive nucleotides selected from within the illustrative preferred target segments are considered to be suitable for targeting as well.

Target segments can include DNA or RNA sequences that comprise at least the 5 consecutive nucleotides from the 5'-terminus of one of the illustrative preferred target segments (the remaining nucleotides being a consecutive stretch of the same DNA or RNA beginning immediately upstream of the 5'-terminus of the target segment and continuing until the DNA or RNA contains about 5 to about 100 nucleotides). Similarly preferred target segments are represented by DNA or RNA sequences that comprise at least the 5 consecutive nucleotides from the 3'-terminus of one of the illustrative preferred target segments (the remaining nucleotides being a consecutive stretch of the same DNA or RNA beginning immediately downstream of the 3'-terminus of the target segment and continuing until the DNA or RNA contains about 5 to about 100 nucleotides). One having skill in the art armed with the target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

In embodiments of the invention the oligonucleotides bind to an antisense strand of a particular target. The oligonucleotides are at least 5 nucleotides in length and can be synthesized so each oligonucleotide targets overlapping sequences such that oligonucleotides are synthesized to cover the entire length of the target polynucleotide. The targets also include coding as well as non coding regions.

In one embodiment, it is preferred to target specific nucleic acids by antisense oligonucleotides. Targeting an antisense compound to a particular nucleic acid is a multi-step process. The process usually begins with the identification of a nucleic acid sequence whose function is to be modulated. This may be, for example, a cellular gene (or mRNA transcribed from the gene) whose expression is associated with a particular disorder or disease state, or a non coding polynucleotide such as for example, non coding RNA (ncRNA).

RNAs can be classified into (1) messenger RNAs (mRNAs), which are translated into proteins, and (2) non-protein-coding RNAs (ncRNAs), ncRNAs comprise micro-RNAs, antisense transcripts and other Transcriptional Units (TU) containing a high density of stop codons and lacking any extensive "Open Reading Frame". Many ncRNAs appear to start from initiation sites in 3' untranslated regions (3'UTRs) of protein-coding loci. ncRNAs are often rare and at least half of the ncRNAs that have been sequenced by the FANTOM consortium seem not to be polyadenylated. Most researchers have for obvious reasons focused on polyadenylated mRNAs that are processed and exported to the cytoplasm. Recently, it was shown that the set of non-polyadenylated nuclear RNAs may be very large, and that many such transcripts arise from so-called intergenic regions. The mechanism by which ncRNAs may regulate gene expression is by base pairing with target transcripts. The RNAs that function by base pairing can be grouped into (1) cis encoded RNAs that are encoded at the same genetic location, but on the opposite strand to the RNAs they act upon and therefore display perfect complementarity to their target, and (2) trans-encoded RNAs that are encoded at a chromosomal location distinct from the RNAs they act upon and generally do not exhibit perfect base-pairing potential with their targets.

Without wishing to be bound by theory, perturbation of an antisense polynucleotide by the antisense oligonucleotides described herein can alter the expression of the corresponding sense messenger RNAs. However, this regulation can either be discordant (antisense knockdown results in messenger RNA elevation) or concordant (antisense knockdown results in concomitant messenger RNA reduction). In these cases, antisense oligonucleotides can be targeted to overlapping or non-overlapping parts of the antisense transcript resulting in its knockdown or sequestration. Coding as well as non-coding antisense can be targeted in an identical manner and that either category is capable of regulating the corresponding sense transcripts—either in a concordant or disconcordant manner. The strategies that are employed in identifying new oligonucleotides for use against a target can be based on the knockdown of antisense RNA transcripts by antisense oligonucleotides or any other means of modulating the desired target.

Strategy 1:

In the case of discordant regulation, knocking down the antisense transcript elevates the expression of the conventional (sense) gene. Should that latter gene encode for a known or putative drug target, then knockdown of its antisense counterpart could conceivably mimic the action of a receptor agonist or an enzyme stimulant.

Strategy 2:

In the case of concordant regulation, one could concomitantly knock down both antisense and sense transcripts and thereby achieve synergistic reduction of the conventional (sense) gene expression. If, for example, an antisense oligonucleotide is used to achieve knockdown, then this strategy can be used to apply one antisense oligonucleotide targeted to the sense transcript and another antisense oligonucleotide to the corresponding antisense transcript, or a single energetically symmetric antisense oligonucleotide that simultaneously targets overlapping sense and antisense transcripts.

According to the present invention, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, doublestranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression or function is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

In an embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

dsRNA can also activate gene expression, a mechanism that has been termed "small RNA-induced gene activation" or RNAa. dsRNAs targeting gene promoters induce potent transcriptional activation of associated genes. RNAa was demonstrated in human cells using synthetic dsRNAs, termed "small activating RNAs" (saRNAs). It is currently not known whether RNAa is conserved in other organisms.

Small double-stranded RNA (dsRNA), such as small interfering RNA (siRNA) and microRNA (miRNA), have been found to be the trigger of an evolutionary conserved mechanism known as RNA interference (RNAi). RNAi invariably leads to gene silencing via remodeling chromatin to thereby suppress transcription, degrading complementary mRNA, or blocking protein translation. However, in instances described in detail in the examples section which follows, oligonucleotides are shown to increase the expression and/or function of the Alpha-L-Iduronidase (IDUA) polynucleotides and encoded products thereof. dsRNAs may also act as small activating RNAs (saRNA). Without wishing to be bound by theory, by targeting sequences in gene promoters, saRNAs would induce target gene expression in a phenomenon referred to as dsRNA-induced transcriptional activation (RNAa).

In a further embodiment, the "preferred target segments" identified herein may be employed in a screen for additional compounds that modulate the expression of Alpha-L-Iduronidase (IDUA) polynucleotides. "Modulators" are those compounds that decrease or increase the expression of a nucleic acid molecule encoding IDUA and which comprise at least a 5-nucleotide portion that is complementary to a preferred target segment. The screening method comprises the steps of contacting a preferred target segment of a nucleic acid molecule encoding sense or natural antisense polynucleotides of IDUA with one or more candidate modulators, and selecting for one or more candidate modulators which decrease or increase the expression of a nucleic acid molecule encoding IDUA polynucleotides, e.g. SEQ ID NOS: 10 to 28. Once it is shown that the candidate modulator or modulators are capable of modulating (e.g. either decreasing or increasing) the expression of a nucleic acid molecule encoding IDUA polynucleotides, the modulator may then be employed in further investigative studies of the function of IDUA polynucleotides, or for use as a research, diagnostic, or therapeutic agent in accordance with the present invention.

Targeting the natural antisense sequence preferably modulates the function of the target gene. For example, the IDUA gene (e.g. accession number NM_000203). In an embodiment, the target is an antisense polynucleotide of the IDUA gene. In an embodiment, an antisense oligonucleotide targets sense and/or natural antisense sequences of IDUA polynucleotides (e.g. accession number NM_000203), variants, alleles, isoforms, homologs, mutants, derivatives, fragments and complementary sequences thereto. Preferably the oligonucleotide is an antisense molecule and the targets include coding and noncoding regions of antisense and/or sense IDUA polynucleotides.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications. For example, such double-stranded moieties have been shown to inhibit the target by the classical hybridization of antisense strand of the duplex to the target, thereby triggering enzymatic degradation of the target.

In an embodiment, an antisense oligonucleotide targets Alpha-L-Iduronidase (IDUA) polynucleotides (e.g. accession number NM_000203), variants, alleles, homologs, mutants, derivatives, fragments and complementary sequences thereto. Preferably the oligonucleotide is an antisense molecule.

In accordance with embodiments of the invention, the target nucleic acid molecule is not limited to IDUA alone but extends to any polynucleotide variant thereof and any polynucleotide that produces, affects, impacts or results in or relates to an IDUA expression product and/or any isoforms thereof.

In an embodiment, an oligonucleotide targets a natural antisense sequence of IDUA polynucleotides, for example, polynucleotides set forth as SEQ ID NOS: 2 to 9, and any variants, alleles, homologs, mutants, derivatives, fragments and complementary sequences thereto. Examples of antisense oligonucleotides are set forth as SEQ ID NOS: 10 to 28.

In one embodiment, the oligonucleotides are complementary to or bind to nucleic acid sequences of IDUA antisense, including without limitation noncoding sense and/or antisense sequences associated with IDUA polynucleotides and modulate expression and/or function of IDUA molecules.

In an embodiment, the oligonucleotides are complementary to or bind to nucleic acid sequences of IDUA natural antisense, set forth as SEQ ID NOS: 2 to 9, and modulate expression and/or function of IDUA molecules.

In an embodiment, oligonucleotides comprise sequences of at least 5 consecutive nucleotides of SEQ ID NOS: 10 to 28 and modulate expression and/or function of IDUA molecules.

The polynucleotide targets comprise IDUA, including family members thereof, variants of IDUA; mutants of IDUA, including SNPs; noncoding sequences of IDUA; alleles of IDUA; species variants, fragments and the like. Preferably the oligonucleotide is an antisense molecule.

In an embodiment, the oligonucleotide targeting IDUA polynucleotides, comprise: antisense RNA, interference RNA (RNAi), short interfering RNA (siRNA); micro interfering RNA (miRNA); a small, temporal RNA (stRNA); or a short, hairpin RNA (shRNA): small RNA-induced gene activation (RNAa); or, small activating RNA (saRNA).

In an embodiment, targeting of Alpha-L-Iduronidase (IDUA) polynucleotides, e.g. SEQ ID NOS: 2 to 28 modulate the expression or function of these targets. In one embodiment, expression or function is up-regulated as compared to a control. In an embodiment, expression or function is down-regulated as compared to a control.

In an embodiment, antisense compounds comprise sequences set forth as SEQ ID NOS: 10 to 28. These oligonucleotides can comprise one or more modified nucleotides, shorter or longer fragments, modified bonds and the like.

In an embodiment, SEQ ID NOS: 10 to 28 comprise one or more LNA nucleotides. Table 1 shows exemplary antisense oligonucleotides useful in the methods of the invention.

peutic agents for human disease. Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

In general, enzymatic nucleic acids with RNA cleaving activity act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its

TABLE 1

| Sequence ID | Antisense Sequence Name | Sequence |
| --- | --- | --- |
| SEQ ID NO: 10 | CUR-1820 | T*C*T*C*T*C*G*C*C*T*T*T*C*C*C*T*C*C*T |
| SEQ ID NO: 11 | CUR-1821 | C*T*C*A*A*G*C*A*A*T*C*T*C*C*A*C*C*T*C*A |
| SEQ ID NO: 12 | CUR-1822 | T*C*C*C*A*G*C*T*A*C*T*C*A*G*A*G*G*C*T |
| SEQ ID NO: 13 | CUR-1823 | C*A*T*G*T*C*T*T*G*T*G*T*G*G*C*T*G*G*A*T |
| SEQ ID NO: 14 | CUR-1973 | G*A*G*T*C*A*T*C*G*T*C*C*T*C*A*G*A*G*C*A*G |
| SEQ ID NO: 15 | CUR-1975 | A*T*T*C*T*C*C*T*T*C*C*T*G*C*T*A*A*A*G*C |
| SEQ ID NO: 16 | CUR-1976 | A*T*T*A*T*T*T*C*G*T*A*T*T*G*C*T*T*T*G*G*C |
| SEQ ID NO: 17 | CUR-1978 | C*A*C*A*C*A*T*G*C*A*T*A*C*A*T*G*G*A*C*T |
| SEQ ID NO: 18 | CUR-1981 | C*T*C*A*G*T*T*C*T*C*T*G*A*C*G*C*T*T*T*G*A*G |
| SEQ ID NO: 19 | CUR-1984 | G*C*C*A*C*A*G*T*G*T*G*A*G*G*A*A*C*G |
| SEQ ID NO: 20 | CUR-1985 | G*T*A*A*T*A*A*T*T*T*T*C*C*T*G*A*C*C*C |
| SEQ ID NO: 21 | CUR-1987 | A*G*T*C*G*T*T*T*A*A*T*A*A*T*T*C*T*G*G*A*G*T |
| SEQ ID NO: 22 | CUR-1988 | T*T*A*C*T*A*A*G*T*T*T*C*A*T*G*A*G*G*T*T |
| SEQ ID NO: 23 | CUR-1974 | A*T*G*G*C*T*C*A*A*C*T*C*A*C*A*T*A*G*C*A |
| SEQ ID NO: 24 | CUR-1977 | T*T*A*T*A*C*A*A*T*G*T*T*T*G*C*T*T*G*G*A*T*T |
| SEQ ID NO: 25 | CUR-1986 | T*T*G*T*T*G*C*A*C*A*A*T*G*T*A*C*A*A*G |
| SEQ ID NO: 26 | CUR-1983 | T*G*G*T*T*G*C*T*C*T*C*A*G*G*A*G*G*C*G*G*C*T |
| SEQ ID NO: 27 | CUR-1979 | A*T*T*T*T*A*G*T*T*G*T*T*T*T*C*T*C*T*G*G |
| SEQ ID NO: 28 | CUR-1982 | C*A*C*G*G*T*G*T*G*G*G*A*C*T*G*G*T*G*G*T |

The modulation of a desired target nucleic acid can be carried out in several ways known in the art. For example, antisense oligonucleotides, siRNA etc. Enzymatic nucleic acid molecules (e.g., ribozymes) are nucleic acid molecules capable of catalyzing one or more of a variety of reactions, including the ability to repeatedly cleave other separate nucleic acid molecules in a nucleotide base sequence-specific manner. Such enzymatic nucleic acid molecules can be used, for example, to target virtually any RNA transcript.

Because of their sequence-specificity, trans-cleaving enzymatic nucleic acid molecules show promise as thera- RNA target, it is released from that RNA to search for another target and can repeatedly bind and cleave new targets.

Several approaches such as in vitro selection (evolution) strategies (Orgel, (1979) Proc. R. Soc. London, B 205, 435) have been used to evolve new nucleic acid catalysts capable of catalyzing a variety of reactions, such as cleavage and ligation of phosphodiester linkages and amide linkages.

The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min-1 in the presence of saturating (10 mM) concentrations of Mg2+ cofactor. An artificial "RNA ligase" ribozyme has been shown to catalyze the corresponding self-modification reaction with a rate of about 100 min-1. In addition, it is known that certain modified hammerhead ribozymes that have substrate binding arms made of DNA catalyze RNA cleavage with multiple turn-over rates that approach 100 min-1. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural self-cleaving ribozymes. It is then possible that the structures of certain selfcleaving ribozymes may be optimized to give maximal catalytic activity, or that entirely new RNA motifs can be made that display significantly faster rates for RNA phosphodiester cleavage.

Intermolecular cleavage of an RNA substrate by an RNA catalyst that fits the "hammerhead" model was first shown in 1987 (Uhlenbeck, O. C. (1987) Nature, 328: 596-600). The RNA catalyst was recovered and reacted with multiple RNA molecules, demonstrating that it was truly catalytic.

Catalytic RNAs designed based on the "hammerhead" motif have been used to cleave specific target sequences by making appropriate base changes in the catalytic RNA to maintain necessary base pairing with the target sequences. This has allowed use of the catalytic RNA to cleave specific target sequences and indicates that catalytic RNAs designed according to the "hammerhead" model may possibly cleave specific substrate RNAs in vivo.

RNA interference (RNAi) has become a powerful tool for modulating gene expression in mammals and mammalian cells. This approach requires the delivery of small interfering RNA (siRNA) either as RNA itself or as DNA, using an expression plasmid or virus and the coding sequence for small hairpin RNAs that are processed to siRNAs. This system enables efficient transport of the pre-siRNAs to the cytoplasm where they are active and permit the use of regulated and tissue specific promoters for gene expression.

In an embodiment, an oligonucleotide or antisense compound comprises an oligomer or polymer of ribonucleic acid (RNA) and/or deoxyribonucleic acid (DNA) or a mimetic, chimera, analog or homolog thereof. This term includes oligonucleotides composed of naturally occurring nucleotides, sugars and covalent internucleoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

According to the present invention, the oligonucleotides or "antisense compounds" include antisense oligonucleotides (e.g. RNA, DNA, mimetic, chimera, analog or homolog thereof), ribozymes, external guide sequence (EGS) oligonucleotides, siRNA compounds, single- or double-stranded RNA interference (RNAi) compounds such as siRNA compounds, saRNA, aRNA, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally, U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

The antisense compounds in accordance with this invention can comprise an antisense portion from about 5 to about 80 nucleotides (i.e. from about 5 to about 80 linked nucleosides) in length. This refers to the length of the antisense strand or portion of the antisense compound. In other words, a single-stranded antisense compound of the invention comprises from 5 to about 80 nucleotides, and a double-stranded antisense compound of the invention (such as a dsRNA, for example) comprises a sense and an antisense strand or portion of 5 to about 80 nucleotides in length. One of ordinary skill in the art will appreciate that this comprehends antisense portions of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides in length, or any range therewithin.

In one embodiment, the antisense compounds of the invention have antisense portions of 10 to 50 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length.

In one embodiment, the antisense or oligonucleotide compounds of the invention have antisense portions of 12 or 13 to 30 nucleotides in length. One having ordinary skill in the an will appreciate that this embodies antisense compounds having antisense portions of 12, 13, 14, 15, 16, 17, 18, 19, 20, 21, 22, 23, 24, 25, 26, 27, 28, 29 or 30 nucleotides in length, or any range therewithin.

In an embodiment, the oligomeric compounds of the present invention also include variants in which a different base is present at one or more of the nucleotide positions in the compound. For example, if the first nucleotide is an adenosine, variants may be produced which contain thymidine, guanosine or cytidine at this position. This may be done at any of the positions of the antisense or dsRNA compounds. These compounds are then tested using the methods described herein to determine their ability to inhibit expression of a target nucleic acid.

In some embodiments, homology, sequence identity or complementarity, between the antisense compound and target is from about 40% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In an embodiment, the antisense oligonucleotides, such as for example, nucleic acid molecules set forth in SEQ ID NOS: 10 to 28 comprise one or more substitutions or modifications. In one embodiment, the nucleotides are substituted with locked nucleic acids (LNA).

In an embodiment, the oligonucleotides target one or more regions of the nucleic acid molecules sense and/or antisense of coding and/or non-coding sequences associated with IDUA and the sequences set forth as SEQ ID NOS: 1 to 9. The oligonucleotides are also targeted to overlapping regions of SEQ ID NOS: 1 to 9.

Certain preferred oligonucleotides of this invention are chimeric oligonucleotides. "Chimeric oligonucleotides" or "chimeras," in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense modulation of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one an embodiment, a chimeric oligonucleotide comprises at least one region modified to increase target binding affinity, and, usually, a region that acts as a substrate for RNAse H. Affinity of an oligonucleotide for its target (min this case, a nucleic acid encoding ras) is routinely determined by measuring the Tm of an oligonucleotide/target pair, which is the temperature at which the oligonucleotide and target dissociate; dissociation is detected spectrophotometrically. The higher the Tm, the greater is the affinity of the oligonucleotide for the target.

Chimeric antisense compounds of the invention may be formed as composite structures of two or more oligonucleotides, modified oligonucleotides, oligonucleosides and/or oligonucleotides mimetics as described above. Such; compounds have also been referred to in the art as hybrids or gapmers. Representative United States patents that teach the preparation of such hybrid structures comprise, but are not limited to, U.S. Pat. Nos. 5,013,830; 5,149,797; 5, 220,007; 5,256,775; 5,366,878; 5,403,711; 5,491,133; 5,565,350; 5,623,065; 5,652,355; 5,652356; and 5,700,922, each of which is herein incorporated by reference.

In an embodiment, the region of the oligonucleotide which is modified comprises at least one nucleotide modified at the 2' position of the sugar, most preferably a 2'-Oalkyl, 2'-O-alkyl-O-alkyl or 2'-fluor-modified nucleotide. In other an embodiment, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target. The effect of such increased affinity is to greatly enhance RNAi oligonucleotide inhibition of gene expression. RNAse H is a cellular endonuclease that cleaves the RNA strand of RNA:DNA duplexes; activation of this enzyme therefore results in cleavage of the RNA target, and thus can greatly enhance the efficiency of RNAi inhibition. Cleavage of the RNA target can be routinely demonstrated by gel electrophoresis. In an embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance.

Specific examples of some preferred oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, —N(CH3)-O—CH2 [known as a methylene (methylimino) or MMI backbone], CH2-O—N(CH3)-CH2, CH2-N(CH3)-N(CH3)-CH2 and O—N(CH3)-CH2-CH2 backbones, wherein the native phosphodiester backbone is represented as O—P—O—CH). The amide backbones disclosed by De Mesmacker et al. (1995) Ace. Chem. Res. 28:366-374 are also preferred. Also preferred are oligonucleotides having morpholino backbone structures (Summerton and Weller, U.S. Pat. No. 5,034,506). In other an embodiment, such as the peptide nucleic acid (PNA) backbone, the phosphodiester backbone of the oligonucleotide is replaced with a polyamide backbone, the nucleotides being bound directly or indirectly to the aza nitrogen atoms of the polyamide backbone. Oligonucleotides may also comprise one or more substituted sugar moieties. Preferred oligonucleotides comprise one of the following at the 2' position: OH, SH, SCH3, F, OCN, OCH3, O(CH2)n CH3, O(CH2)n NH2 or O(CH2)n CH3 where n is from 1 to about 10; C1 to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH2 CH2 OCH3, also known as 2'-O-(2-methoxyethyl)]. Other preferred modifications include 2'-methoxy (2'-O—CH3), 2'-propoxy (2'-OCH2 CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleotides include adenine (A), guanine (G), thymine (T), cytosine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as S-Me-C), 5-hydroxymethylcytosine (HMC), glycosyl HMC and gentobiosyl HMC, as well as synthetic nucleotides, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. A "universal" base known in the art, e.g., inosine, may be included. 5-Me-C substitutions have been shown to increase nucleic acid duplex stability by 0.6-1.2° C. and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety, an aliphatic chain, e.g., dodecandiol or undecyl residues, a polyamine or a polyethylene glycol chain, or Adamantane acetic acid. Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In accordance with the invention, use of modifications such as the use of LNA monomers to enhance the potency, specificity and duration of action and broaden the routes of administration of oligonuclotides comprised of current chemistries such as MOE, ANA, FANA, PS etc. This can be achieved by substituting some of the monomers in the current oligonucleotides by LNA monomers. The LNA modified oligonucleotide may have a size similar to the parent compound or may be larger or preferably smaller. It is preferred that such LNA-modified oligonucleotides contain less than about 70%, more preferably less than about 60%, most preferably less than about 50% LNA monomers and that their sizes are between about 5 and 25 nucleotides, more preferably between about 12 and 20 nucleotides.

Preferred modified oligonucleotide backbones comprise, but not limited to, phosphorothioates, chiral phosphorothioates, phosphorodithioates, phosphotriesters, aminoalkylphosphotriestrs, methyl and other alkyl phosphonates comprising 3' alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus containing linkages comprise, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131;

5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones, methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleosides comprise, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen, et al. (1991) Science 254, 1497-1500.

In an embodiment of the invention the oligonucleotides with phosphorothioate backbones and oligonucleosides with heteroatom backbones, and in particular —CH2-NH—O-CH2-, —CH2-N(CH3)-O—CH2-known as a methylene (methylimino) or MMI backbone, —CH2-O—N(CH3)-CH2-, —CH2N(CH3)-N(CH3) CH2- and —O—N(CH3)-CH2-CH2- wherein the native phosphodiester backbone is represented as —O—P—O—CH2- of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O(CH2)n OmCH3, O(CH2)n, OCH3, O(CH2)nNH2, O(CH2)nCH3, O(CH2)nONH2, and O(CH2)nON(CH3)2 where n and m can be from 1 to about 10. Other preferred oligonucleotides comprise one of the following at the 2' position: C to CO, (lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification comprises 2'-methoxyethoxy (2'-O—CH2CH2OCH3, also known as 2'-O-(2-methoxyethyl) or 2'-MOE) i.e., an alkoxyalkoxy group. A further preferred modification comprises 2'-dimethylaminooxyethoxy, i.e., a O(CH2)2ON(CH3)2 group, also known as 2'-DMAOE, as described in examples herein below, and 2'-dimethylaminoethoxyethoxy (also known in the an as 2'-O-dimethylaminoethoxyethyl or 2'-DMAEOE), i.e., 2'-O—CH2-O—CH2-N(CH2)2.

Other preferred modifications comprise 2'-methoxy (2'-O CH3), 2'-aminopropoxy (2'-CH2CH2CH2NH2) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures comprise, but are not limited to, U.S. Pat. Nos. 4,981,957; 5,118,800; 5,319,080; 5,359,044; 5,393,878; 5,446,137; 5,466,786; 5,514, 785; 5,519,134; 5,567,811; 5,576,427; 5,591,722; 5,597,909; 5,610,300; 5,627,053; 5,639,873; 5,646, 265; 5,658,873; 5,670,633; and 5,700,920, each of which is herein incorporated by reference.

Oligonucleotides may also comprise nucleobase (often referred to in the art simply as "base") modifications or substitutions. As used herein, "unmodified" or "natural" nucleotides comprise the purine bases adenine (A) and guanine (G), and the pyrimidine bases thymine (T), cytosine (C) and uracil (U). Modified nucleotides comprise other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

Further, nucleotides comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by English et al., 'Angewandle Chemie, International Edition', 1991, 30, page 613, and those disclosed by Sanghvi, Y. S., Chapter 15, 'Antisense Research and Applications', pages 289-302, Crooke, S. T. and Lebleu, B. ea., CRC Press, 1993. Certain of these nucleotides are particularly useful for increasing the binding affinity of the oligomeric compounds of the invention. These comprise 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-12° C. (Sanghvi, Y. S., Crooke, S. T. and Lebleu. B., eds, 'Antisense Research and Applications', CRC Press. Boca Raton, 1993, pp. 276-278) and are presently preferred base substitutions, even more particularly when combined with 2'-Omethoxyethyl sugar modifications.

Representative United States patents that teach the preparation of the above noted modified nucleotides as well as other modified nucleotides comprise, but are not limited to, U.S. Pat. No. 3,687,808, as well as U.S. Pat. Nos. 4,845,205; 5,130,302; 5,134,066; 5,175,273; 5, 367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

Another modification of the oligonucleotides of the invention involves chemically linking to the oligonucleotide one or more moieties or conjugates, which enhance the activity, cellular distribution, or cellular uptake of the oligonucleotide.

Such moieties comprise but are not limited to, lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or Adamantane acetic acid, a palmityl moiety, or an octadecylamine or hexylamino-carbonyl-t oxycholesterol moiety.

Representative United States patents that teach the preparation of such oligonucleotides conjugates comprise, but are not limited to, U.S. Pat. Nos. 4,828,979; 4,948,882; 5,218, 105; 5,525,465; 5,541,313; 5,545,730; 5,552, 538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599, 928 and 5,688,941, each of which is herein incorporated by reference.

Drug Discovery:

The compounds of the present invention can also be applied in the areas of drug discovery and target validation. The present invention comprehends the use of the compounds and preferred target segments identified herein in drug discovery efforts to elucidate relationships that exist between Alpha-L-Iduronidase (IDUA) polynucleotides and a disease state, phenotype, or condition. These methods include detecting or modulating IDUA polynucleotides comprising contacting a sample, tissue, cell, or organism with the compounds of the present invention, measuring the nucleic acid or protein level of IDUA polynucleotides and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

Assessing Up-Regulation or Inhibition of Gene Expression:

Transfer of an exogenous nucleic acid into a host cell or organism can be assessed by directly detecting the presence of the nucleic acid in the cell or organism. Such detection can be achieved by several methods well known in the art. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods including gene expression analysis. For instance, mRNA produced from an exogenous nucleic acid can be detected and quantified using a Northern blot and reverse transcription PCR (RT-PCR).

Expression of RNA from the exogenous nucleic acid can also be detected by measuring an enzymatic activity or a reporter protein activity. For example, antisense modulatory activity can be measured indirectly as a decrease or increase in target nucleic acid expression as an indication that the exogenous nucleic acid is producing the effector RNA. Based on sequence conservation, primers can be designed and used to amplify coding regions of the target genes. Initially, the most highly expressed coding region from each gene can be used to build a model control gene, although any coding or non coding region can be used. Each control gene is assembled by inserting each coding region between a reporter coding region and its poly(A) signal. These plasmids would produce an mRNA with a reporter gene in the upstream portion of the gene and a potential RNAi target in the 3' non-coding region. The effectiveness of individual antisense oligonucleotides would be assayed by modulation of the reporter gene. Reporter genes useful in the methods of the present invention include acetohydroxyacid synthase (AHAS), alkaline phosphatase (AP), beta galactosidase (LacZ), beta glucuronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS) and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

IDUA protein and mRNA expression can be assayed using methods known to those of skill in the art and described elsewhere herein. For example, immunoassays such as the ELISA can be used to measure protein levels. IDUA ELISA assay kits are available commercially, e.g., from R&D Systems (Minneapolis, Minn.).

In embodiments, IDUA expression (e.g., mRNA or protein) in a sample (e.g., cells or tissues in vivo or in vitro) treated using an antisense oligonucleotide of the invention is evaluated by comparison with IDUA expression in a control sample. For example, expression of the protein or nucleic acid can be compared using methods known to those of skill in the art with that in a mock-treated or untreated sample. Alternatively, comparison with a sample treated with a control antisense oligonucleotide (e.g., one having an altered or different sequence) can be made depending on the information desired. In another embodiment, a difference in the expression of the IDUA protein or nucleic acid in a treated vs. an untreated sample can be compared with the difference in expression of a different nucleic acid (including any standard deemed appropriate by the researcher, e.g., a housekeeping gene) in a treated sample vs. an untreated sample.

Observed differences can be expressed as desired, e.g., in the form of a ratio or fraction, for use in a comparison with control. In embodiments, the level of IDUA mRNA or protein, in a sample treated with an antisense oligonucleotide of the present invention, is increased or decreased by about 1.25-fold to about 10-fold or more relative to an untreated sample or a sample treated with a control nucleic acid. In embodiments, the level of IDUA mRNA or protein is increased or decreased by at least about 1.25-fold, at least about 1.3-fold, at least about 1.4-fold, at least about 1.5-fold, at least about 1.6-fold, at least about 1.7-fold, at least about 1.8-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or at least about 10-fold or more.

Kits, Research Reagents, Diagnostics, and Therapeutic

The compounds of the present invention can be utilized for diagnostics, therapeutics, and prophylaxis, and as research reagents and components of kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics and in various biological systems, the compounds of the present invention, either alone or in combination with other compounds or therapeutics, are useful as tools in differential and/or combinatorial analyses to elucidate expression patterns of a portion or the entire complement of genes expressed within cells and tissues.

As used herein the term "biological system" or "system" is defined as any organism, cell, cell culture or tissue that expresses, or is made competent to express products of the Alpha-L-Iduronidase (IDUA) genes. These include, but are not limited to, humans, transgenic animals, cells, cell cultures, tissues, xenografts, transplants and combinations thereof.

As one non limiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays, SAGE (serial analysis of gene expression), READS (restriction enzyme amplification of digested cDNAs), TOGA (total gene expression analysis), protein arrays and proteomics, expressed sequence tag (EST) sequencing, subtractive RNA fingerprinting (SuRF), subtractive cloning, differential display (DD), comparative genomic hybridization, FISH (fluorescent in situ hybridization) techniques and mass spectrometry methods.

The compounds of the invention are useful for research and diagnostics, because these compounds hybridize to nucleic acids encoding Alpha-L-Iduronidase (IDUA). For example, oligonucleotides that hybridize with such efficiency and under such conditions as disclosed herein as to be effective IDUA modulators are effective primers or probes under conditions favoring gene amplification or detection, respectively. These primers and probes are useful in methods requiring the specific detection of nucleic acid molecules encoding IDUA and in the amplification of said nucleic acid molecules for detection or for use in further studies of IDUA. Hybridization of the antisense oligonucleotides, particularly the primers and probes, of the invention with a nucleic acid encoding IDUA can be detected by means known in the art. Such means may include conjugation of an enzyme to the oligonucleotide, radiolabeling of the oligonucleotide, or any other suitable detection means. Kits using such detection means for detecting the level of IDUA in a sample may also be prepared.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of IDUA polynucleotides is treated by administering antisense compounds in accordance with this invention. For example, in one non-limiting embodiment, the methods comprise the step of administering to the animal in need of treatment, a therapeutically effective amount of IDUA modulator. The IDUA modulators of the present invention effectively modulate the activity of the IDUA or modulate the expression of the IDUA protein. In one embodiment, the activity or expression of IDUA in an animal is inhibited by about 10% as compared to a control. Preferably, the activity or expression of IDUA in an animal is inhibited by about 30%. More preferably, the activity or expression of IDUA in an animal is inhibited by 50% or more. Thus, the oligomeric compounds modulate expression of Alpha-L-Iduronidase (IDUA) mRNA by at least 10%, by at least 50%, by at least 25%, by at least 30%0, by at least 40%, by at least 50%, by at least 60%, by at least 70%, by at least 75%, by at least 80%, by at least 85%, by at least 90%, by at least 95%, by at least 98%, by at least 99% or by 100% as compared to a control.

In one embodiment, the activity or expression of Alpha-L-Iduronidase (IDUA) in an animal is increased by about 10% as compared to a control. Preferably, the activity or expression of IDUA in an animal is increased by about 30%. More preferably, the activity or expression of IDUA in an animal is increased by 50% or more. Thus, the oligomeric compounds modulate expression of IDUA mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

For example, the increase or reduction of the expression of Alpha-L-Iduronidase (IDUA) may be measured in serum, blood, adipose tissue, liver or any other body fluid, tissue or organ of the animal. Preferably, the cells contained within said fluids, tissues or organs being analyzed contain a nucleic acid molecule encoding IDUA peptides and/or the IDUA protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

Conjugates

Another modification of the oligonucleotides of the invention involves chemically linking to the oligonucleotide one or more moieties or conjugates that enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-Hphosphonate, a polyamine or a polyethylene glycol chain, or Adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Representative United States patents that teach the preparation of such oligonucleotides conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,165; 5,547,932; 5,583,020; 5,591,721; 4,426,330; 4,534,899, 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Although, the antisense oligonucleotides do not need to be administered in the context of a vector in order to modulate a target expression and/or function, embodiments of the invention relates to expression vector constructs for the expression of antisense oligonucleotides, comprising promoters, hybrid promoter gene sequences and possess a strong constitutive promoter activity, or a promoter activity which can be induced in the desired case.

In an embodiment, invention practice involves administering at least one of the foregoing antisense oligonucleotides with a suitable nucleic acid delivery system. In one embodiment, that system includes a non-viral vector operably linked to the polynucleotide. Examples of such nonviral vectors include the oligonucleotide alone (e.g. any one or more of SEQ ID NOS: 10 to 28) or in combination with a suitable protein, polysaccharide or lipid formulation.

Additionally suitable nucleic acid delivery systems include viral vector, typically sequence from at least one of an adenovirus, adenovirus-associated virus (AAV), helper-dependent adenovirus, retrovirus, or hemagglutinatin virus of Japan-liposome (HVJ) complex. Preferably, the viral vector comprises a strong eukaryotic promoter operably linked to the polynucleotide e.g., a cytomegalovirus (CMV) promoter.

Additionally preferred vectors include viral vectors, fusion proteins and chemical conjugates. Retroviral vectors include Moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector, Adenovirus Vectors and Adeno-associated Virus Vectors.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein by reference.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer, intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

For treating tissues in the central nervous system, administration can be made by, e.g., injection or infusion into the cerebrospinal fluid. Administration of antisense RNA into cerebrospinal fluid is described, e.g., in U.S. Pat. App. Pub. No. 2007/0117772, "Methods for slowing familial ALS disease progression," incorporated herein by reference in its entirety.

When it is intended that the antisense oligonucleotide of the present invention be administered to cells in the central nervous system, administration can be with one or more agents capable of promoting penetration of the subject antisense oligonucleotide across the blood-brain barrier. Injection can be made, e.g., in the entorhinal cortex or hippocampus. Delivery of neurotrophic factors by administration of an adenovirus vector to motor neurons in muscle tissue is described in, e.g., U.S. Pat. No. 6,632,427, "Adenoviral-vector-mediated gene transfer into medullary motor neurons," incorporated herein by reference. Delivery of vectors directly to the brain, e.g., the striatum, the thalamus, the hippocampus, or the substantia nigra, is known in the art and described, e.g., in U.S. Pat. No. 6,756,523, "Adenovirus vectors for the transfer of foreign genes into cells of the central nervous system particularly in brain," incorporated herein by reference. Administration can be rapid as by injection or made over a period of time as by slow infusion or administration of slow release formulations.

The subject antisense oligonucleotides can also be linked or conjugated with agents that provide desirable pharmaceutical or pharmacodynamic properties. For example, the antisense oligonucleotide can be coupled to any substance, known in the art to promote penetration or transport across the blood-brain barrier, such as an antibody to the transferrin receptor, and administered by intravenous injection. The antisense compound can be linked with a viral vector, for example, that makes the antisense compound more effective and/or increases the transport of the antisense compound across the blood-brain barrier. Osmotic blood brain barrier disruption can also be accomplished by, e.g., infusion of sugars including, but not limited to, meso erythritol, xylitol, D(+) galactose, D(+) lactose, D(+) xylose, dulcitol, myo-inositol, L(−) fructose, D(−) mannitol, D(+) glucose. D(+) arabinose, D(−) arabinose, cellobiose, D(+) maltose, D(+) raffinose, L(+) rhamnose, D(+) melibiose, D(−) ribose, adonitol, D(+) arabitol, L(−) arabitol, D(+) fucose, L(−) fucose, D(−) lyxose, L(+) lyxose, and L(−) lyxose, or amino acids including, but not limited to, glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. No. 4,866,042, "Method for the delivery of genetic material across the blood brain barrier," U.S. Pat. No. 6,294,520, "Material for passage through the blood-brain barrier," and U.S. Pat. No. 6,936,589, "Parenteral delivery systems," all incorporated herein by reference in their entirety.

The subject antisense compounds may be admixed, encapsulated, conjugated or otherwise associated with other molecules, molecule structures or mixtures of compounds, for example, liposomes, receptor-targeted molecules, oral, rectal, topical or other formulations, for assisting in uptake, distribution and/or absorption. For example, cationic lipids may be included in the formulation to facilitate oligonucleotide uptake. One such composition shown to facilitate uptake is LIPOFECTIN (available from GIBCO-BRL, Bethesda, Md.).

Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogeneous systems of one liquid dispersed in another in the form of droplets usually exceeding 0.1 μm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids. When incorporated into liposomes, these specialized lipids result in liposomes with enhanced circulation lifetimes relative to liposomeslacking such specialized lipids. Examples of sterically stabilized liposomes are those in which pan of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein by reference.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs Penetration enhancers may be classified as belonging to one of five broad categories, i.e., surfactants, fatty acids, bile salts, chelating agents, and non-chelating nonsurfactants. Penetration enhancers and their uses are further described in U.S. Pat. No. 6,287,860, which is incorporated herein by reference.

One of skill in the an will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoyl-phosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyhetramethylaminopropyl DOTAP and dioleoyl-phosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein by reference. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein by reference.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligonmeric compounds and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bischloroethyl-nitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexyl-nitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclo-phosphoramide, 5-fluorouracil (5-FU), S-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., S-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. For example, the first target may be a particular antisense sequence of Alpha-L-Iduronidase (IDUA), and the second target may be a region from another nucleotide sequence. Alternatively, compositions of the invention may contain two or more antisense compounds targeted to different regions of the same Alpha-L-Iduronidase (IDUA) nucleic acid target. Numerous examples of antisense compounds are illustrated herein and others may be selected from among suitable compounds known in the art. Two or more combined compounds may be used together or sequentially.

Dosing:

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in vitro and in vivo animal models. In general, dosage is from 0.01 µg to about 10 mg per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to about 10 mg per kg of body weight, once or more daily, to once every 2-20 years.

In embodiments, a patient is treated with a dosage of drug that is at least about 1, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 10 mg/kg body weight. Certain injected dosages of antisense oligonucleotides are described, e.g., in U.S. Pat. No. 7,563,884, "Antisense modulation of PTP1B expression," incorporated herein by reference in its entirety. MPS-1 (i.e. mucopolysaccharidosis type 1) is a rare lysosomal storage disease. This disease has three groups of patients with distinct symptoms based on the severity of the disease (Hurler syndrome, Hurler-Scheie syndrome, Scheie syndrome). In studies to determine and support a method of determining and selecting the most preferred oligonucleotide for any individual patient or group of patients having the disease, the following general protocol may be performed. This method may of course use any cells or tissues typically having IDUA polynucleotides and expression products derived therefrom. A patient population may be selected using the following criteria 1, 2; then after acceptance, steps 3, 4, 5 and 6 are performed: (1) The patients with show MPS-1 (i.e. mucopolysaccharidosis type 1) due to a deficiency in IDUA activity. (2) These patients will be defined from medical exam as having a Hurler syndrome or a Hurler-Scheie syndrome or a Scheie syndrome. (3) After patient/guardian consent, a skin biopsy will be taken from the patient; the patient will also be checked for any other diseases (for example infectious diseases) that would require special precautions when handling biological samples from the patient. (4) After full documentation on the patient conditions, the skin biopsy will processed to expand skin fibroblasts in vitro. (5) The skin fibroblasts will be dosed with different concentrations of oligos and different oligos; the oligos are a selected set of oligos complementary to the human IDUA natural antisense that would have been previously characterized as up-regulating the IDUA (mRNA, protein and activity). (6) The percentage increase in IDUA activity is measured from the skin fibroblast cell culture supernatant. NCBI (The National Center for Biotechnology Information) characterizes IDUA activity in different patients (or control) subsets as follows: a patient with two wild type IDUA alleles (IDUA gene from each parent is wild type, meaning has no mutation) the activity of IDUA is 83-121%; Patients with one strong mutation in IDUA (heterozygotes), the IDUA activity is 19 to 60%; Patients with two very strong mutations in IDUA, the total IDUA activity is 0-3%. Heterozygotes are only carriers of the disease and do not show symptoms of the disease. The oligos increasing the IDUA activity to more than about 10% of the total activity seen in normal cells could be considered active drug candidates. Preferably, the percentage increase will be above about 20%. The oligonucleotide with the highest percentage increase in IDUA upregulation is selected as the drug candidate for the individual patient from which the fibroblast measurement was made. The oligonucleotide may also be useful in a subset of patients having the same disease condition or to treat the disease in all of the patients having such disease.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1: Design of Antisense Oligonucleotides Specific for a Nucleic Acid Molecule Antisense to an Alpha-L-Iduronidase (IDUA) and/or a Sense Strand of IDUA Polynucleotide As indicated above the term "oligonucleotide specific for" or "oligonucleotide targets" refers to an oligonucleotide having a sequence (i) capable of forming a stable complex with a portion of the targeted gene, or (ii) capable of forming a stable duplex with a portion of an mRNA transcript of the targeted gene.

Selection of appropriate oligonucleotides is facilitated by using computer programs (e.g. IDT AntiSense Design, IDT OligoAnalyzer) that automatically identify in each given sequence subsequences of 19-25 nucleotides that will form hybrids with a target polynucleotide sequence with a desired melting temperature (usually 50-60° C.) and will not form self-dimers or other complex secondary structures.

Selection of appropriate oligonucleotides is further facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of genes and intergenic regions of a given genome allows the selection of nucleic acid sequences that display an appropriate degree of specificity to the gene of interest. These procedures allow the selection of oligonucleotides that exhibit a high degree of complementarity to target nucleic acid sequences and a lower degree of complementarity to other nucleic acid sequences in a given genome. One skilled in the art will realize that there is considerable latitude in selecting appropriate regions of genes for use in the present invention.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vive assays or therapeutic treatment, and under conditions in which assays are performed in the case of in vitro assays.

The hybridization properties of the oligonucleotides described herein can be determined by one or more in vitro assays as known in the art. For example, the properties of the oligonucleotides described herein can be obtained by determination of binding strength between the target natural antisense and a potential drug molecules using melting curve assay.

The binding strength between the target natural antisense and a potential drug molecule (Molecule) can be estimated using any of the established methods of measuring the strength of intermolecular interactions, for example, a melting curve assay.

Melting curve assay determines the temperature at which a rapid transition from double-stranded to single-stranded conformation occurs for the natural antisense Molecule complex. This temperature is widely accepted as a reliable measure of the interaction strength between the two molecules.

A melting curve assay can be performed using a cDNA copy of the actual natural antisense RNA molecule or a synthetic DNA or RNA nucleotide corresponding to the binding site of the Molecule. Multiple kits containing all necessary reagents to perform this assay are available (e.g. Applied Biosystems Inc. MeltDoctor kit). These kits include a suitable buffer solution containing one of the double strand DNA (dsDNA) binding dyes (such as ABI HRM dyes, SYBR Green, SYTO, etc.). The properties of the dsDNA dyes are such that they emit almost no fluorescence in free form, but are highly fluorescent when bound to dsDNA.

To perform the assay the cDNA or a corresponding oligonucleotide are mixed with Molecule in concentrations defined by the particular manufacturer's protocols. The mixture is heated to 95° C. to dissociate all pre-formed dsDNA complexes, then slowly cooled to room temperature or other lower temperature defined by the kit manufacturer to allow the DNA molecules to anneal. The newly formed complexes are then slowly heated to 95° C. with simultaneous continuous collection of data on the amount of fluorescence that is produced by the reaction. The fluorescence intensity is inversely proportional to the amounts of dsDNA present in the reaction. The data can be collected using a real time PCR instrument compatible with the kit (e.g. ABI's StepOne Plus Real Time PCR System or lighTyper instrument, Roche Diagnostics, Lewes, UK).

Melting peaks are constructed by plotting the negative derivative of fluorescence with respect to temperature (−d (Fluorescence)/dT) on the y-axis) against temperature (x-axis) using appropriate software (for example lightTyper (Roche) or SDS Dissociation Curve, ABI). The data is analyzed to identify the temperature of the rapid transition from dsDNA complex to single strand molecules. This temperature is called Tm and is directly proportional to the strength of interaction between the two molecules. Typically, Tm will exceed 40° C.

Example 2: Modulation of IDUA Polynucleotides

All antisense oligonucleotides used in Example 2 were designed as described in Example 1. The manufacturer (IDT Inc. of Coralville, Iowa) was instructed to manufacture the designed phosphothioate bond oligonucleotides and provided the designed phosphothioate analogs shown in Table 1. The asterisk designation between nucleotides indicates the presence of phosphothioate bond. The oligonucleotides required for the experiment in Example 2 can be synthesized using any appropriate state of the art method, for example the method used by IDT: on solid support, such as a 5 micron controlled pore glass bead (CPG), using phosphoramidite monomers (normal nucleotides with all active groups protected with protection groups, e.g. trityl group on sugar, benzoyl on A and C and N-2-isobutyryl on G). Protection groups prevent the unwanted reactions during oligonucleotide synthesis. Protection groups are removed at the end of the synthesis process. The initial nucleotide is linked to the solid support through the 3' carbon and the synthesis proceeds in the 3' to 5' direction. The addition of a new base to a growing oligonucleotide chain takes place in four steps: 1) the protection group is removed from the 5' oxygen of the immobilized nucleotide using trichloroacetic acid; 2) the immobilized and the next-in-sequence nucleotides are coupled together using tetrazole; the reaction proceeds through a tetrazolyl phosphoramidite intermediate, 3) the unreacted free nucleotides and reaction byproducts are washed away and the unreacted immobilized oligonucleotides are capped to prevent their participation in the next round of synthesis; capping is achieved by acetylating the free 5' hydroxyl using acetic anhydride and N-methyl imidazole; 4) to stabilize the bond between the nucleotides the phosphorus is oxidized using iodine and water, if a phosphodiester bond is to be produced, or Beaucage reagent (3H-1,2-benzodithiol-3-one-1,1-dioxide), if a phosphothioate bond is desired. By alternating the two oxidizing agents, a chimeric backbone can be constructed. The four step cycle described above is repeated for every nucleotide in the sequence. When the complete sequence is synthesized, the oligonucleotide is cleaved from the solid support and deprotected using ammonium hydroxide at high temperature. Protection groups are washed away by desalting and the remaining oligonucleotides are lyophilized.

Treatment of HepG2 Cells with Antisense Oligonucleotides

To perform the experiment designed in Example 2, HepG2 cells from ATCC (cat# HB-8065) were grown in growth media (MEM/EBSS (Hyclone cat #SH30024, or Mediatech cat # MT-10-010-CV)+10% FBS (Mediatech cat#MT35-011-CV)+ penicillin/streptomycin (Mediatech cat# MT30-002-CI)) at 37° C. and 5% CO2. One day before the experiment the cells were replated at the density of 0.5×104/ml into 6 well plates and incubated at 37° C. and 5% CO2 overnight. On the day of the experiment the media in the 6 well plates was changed to fresh growth media.

Oligonucleotides shipped by the manufacturer in lyophilized form were diluted to the concentration of 20 µM in deionized RNAse/DNAse-free water. Two µl of this solution was incubated with 400 µl of OptiMEM media (Gibco cat#31985-070) and 4 µl of Lipofectamine 2000 (Invitrogen cat#11668019) at room temperature for 20 min, then applied dropwise to one well of the 6 well plate with HepG2 cells. Similar mixture including 2 µl of water instead of the oligonucleotide solution was used for the mock-transfected controls. After 3-18 h of incubation at 37° C. and 5% CO2 the media was changed to fresh growth media. 48 h after addition of antisense oligonucleotides the media was removed and RNA was extracted from the cells using SV Total RNA Isolation System from Promega (cat # Z3105) or RNeasy Total RNA Isolation kit from Qiagen (cat#74181) following the manufacturers' instructions. 600 ng of extracted RNA was added to the reverse transcription reaction performed using Verso cDNA kit from Thermo Scientific (cat#AB1453B) or High Capacity cDNA Reverse Transcription Kit (cat#4368813) as described in the manufacturer's protocol. The cDNA from this reverse transcription reaction was used to monitor gene expression by real time PCR using ABI Taqman Gene Expression Mix (cat#4369510) and primers/probes designed by ABI (Applied Biosystems Taqman Gene Expression Assay: Hs00) 164940_m1 (IDUA) by Applied Biosystems Inc. Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems). Fold change in gene expression after treatment with antisense oligonucleotides was calculated based on the difference in 18S-normalized dCt values between treated and mock-transfected samples.

Figure 2:
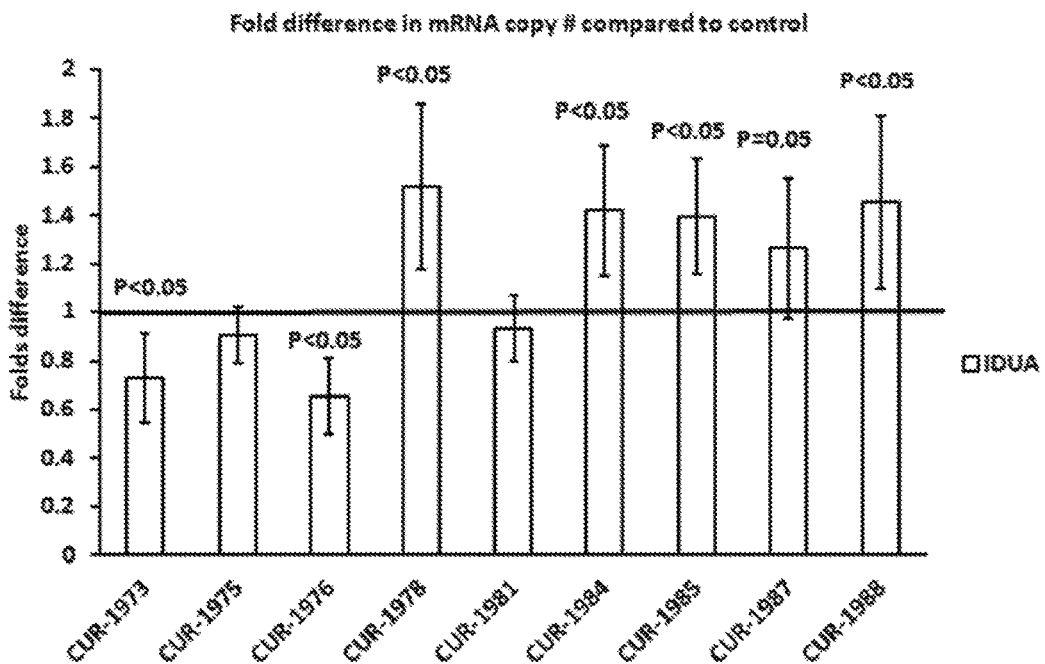
FIG. 2 is a graph of real time PCR results showing the fold change+standard deviation in IDUA mRNA after treatment of HepG2 cells with phosphorothioate oligonucleotides introduced using Lipofectamine™ 2000, as compared to control. Bars denoted as CUR-1973, CUR-1975, CUR-1976, CUR-1978, CUR-1981, CUR-1984, CUR-1985, CUR-1987, CUR-1988 correspond to samples treated with SEQ ID NOS: 14 to 22 respectively.
Figure 3:
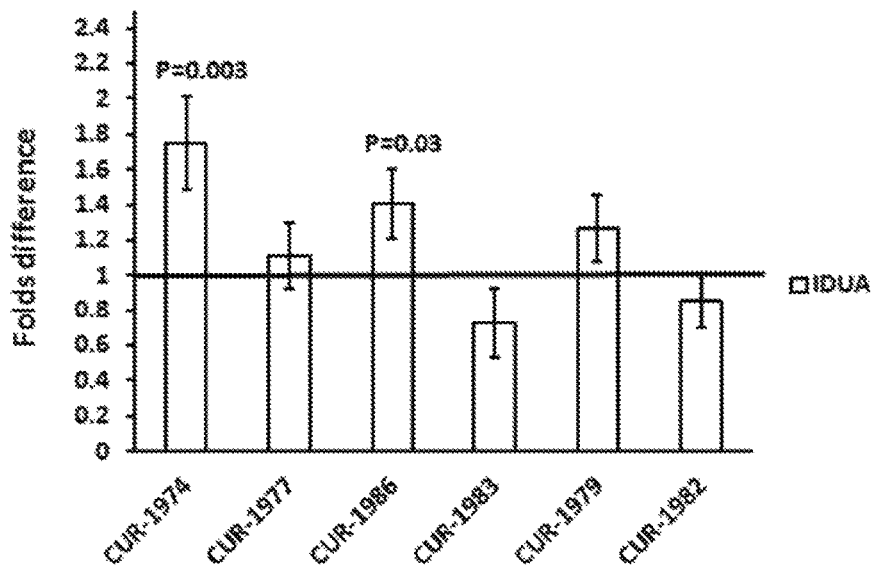
FIG. 3 is a graph of real time PCR results showing the fold change+standard deviation in IDUA mRNA after treatment of HepG2 cells with phosphorothioate oligonucleotides introduced using Lipofectamine™ 2000, as compared to control. Bars denoted as CUR-1974, CUR-1977, CUR-1986, CUR-1983, CUR-1979 and CUR-1982 correspond to samples treated with SEQ ID NOS: 23 to 28 respectively.

Results:

Real Time PCR results show that levels of IDUA mRNA in HepG2 cells are significantly increased 48 h after treatment with the antisense oligonucleotides to human IDUA antisense Hs.656285 with the oligos CUR-1820 and CUR-1821 (FIG. 1), with the oligos CUR-1978, CUR-1984, CUR-1985, CUR-1987 and CUR1988 (FIG. 2), and with the oligos CUR-1974 and CUR-1986 (FIG. 3).

Treatment of SK-N-AS Cell with Antisense Oligonucleotides

In this example SK-N-AS antisense oligonucleotides of different chemistries targeting IDUA-specific natural antisense transcript were screened in human neuroblastoma SK-N-AS cell line at a final concentration of 20 nM.

Materials and Methods:

SK-N-AS cell line. SK-N-AS human neuroblastoma cells from ATCC (cat# CRL-2137) were grown in Growth Media (DMEM (Mediatech cat#10-013-CV)+10% FBS (Mediatech cat# MT35-014)1-CV)+ penicillin/streptomycin (Mediatech cat# MT30-002-CI)+ Non-Essential Amino Acids (NEAA)(HyClone SH30238.01)) at 37° C. and 5% $CO_2$. The cells were treated with antisense oligonucleotides using one of the following methods. For the Next Day Method, one day before the experiment the cells were replated at the density of approximately 3×105/well into 6 well plates in Growth Media and incubated at 37° C. and 5% $CO_2$ overnight. Next day, the media in the 6 well plates was changed to fresh Growth Media (1.5 ml/well) and the cells were dosed with antisense oligonucleotides. All antisense oligonucleotides were manufactured by IDT Inc. (Coralville, Iowa) or Exiqon (Vedbaek, Denmark). The sequences for all oligonucleotides are listed in Table 1. Stock solutions of oligonucleotides were diluted to the concentration of 20 µM in DNAse/RNAse-free sterile water. To dose one well, 1 µl of this solution was incubated with 200 µl of Opti-MEM media (Gibco cat#31985-070) and 2 Hp of Lipofectamine 2000 (Invitrogen cat#11668019) at room temperature for 20 min and applied dropwise to one well of a 24 well plate with cells. Similar mixture including 1 µl of water instead of the oligonucleotide solution was used for the mock-transfected controls. After about 18 h of incubation at 37° C. and 5% CO2 the media was changed to fresh Growth Media. Forty eight hours after addition of antisense oligonucleotides the media was removed and RNA was extracted from the cells using SV Total RNA Isolation System from Promega (cat # Z3105) following the manufacturers' instructions. Six hundred nanograms of purified total RNA was added to the reverse transcription reaction performed using SuperScript VILO cDNA Synthesis Kit from Invitrogen (cat#11754-250) as described in the manufacturer's protocol. The cDNA from this reverse transcription reaction was used to monitor gene expression by real time PCR using ABI Taqman Gene Expression Mix (cat#4369510) and primers/probes designed by ABI (assays Hs00164940_m1). Results obtained using all three assays were very similar. The following PCR cycle was used: 50° C. for 2 min, 95° C. for 10 min, 40 cycles of (95° C. for 15 seconds, 60° C. for 1 min) using StepOne Plus Real Time PCR system (Applied Biosystems). The assay for 18S was manufactured by ABI (cat#4319413E). Fold change in gene expression after treatment with antisense oligonucleotides was calculated based on the difference in 18S-normalized dCt values between treated and mock-transfected samples.

Figure 4:
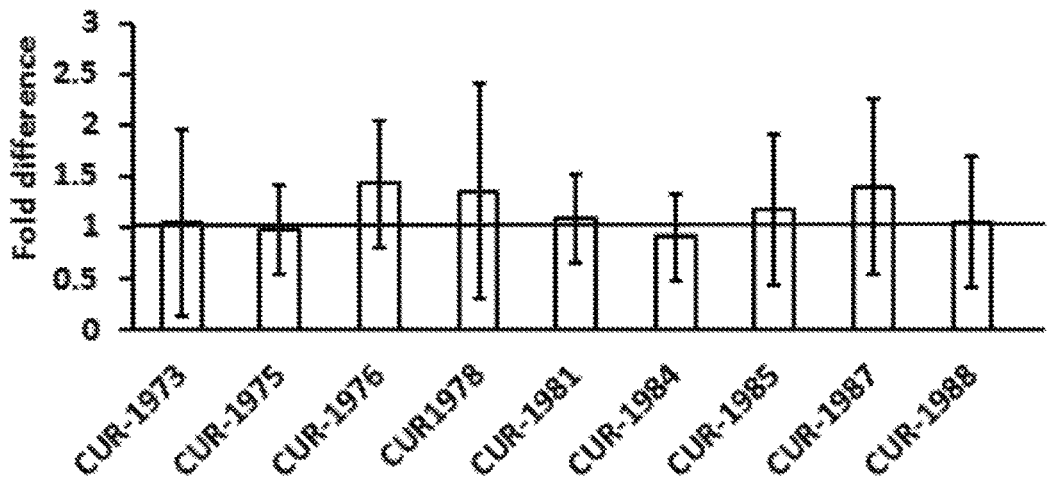
FIG. 4 is a graph of real time PCR results showing the fold change+standard deviation in human IDUA mRNA after treatment of SK-N-As cells with phosphorothioate oligonucleotides introduced using Lipofectamine™ 2000, as compared to control. Bars denoted as CUR-1973, CUR-1975, CUR-1976, CUR-1978, CUR-1981, CUR-1984, CUR-1985, CUR-1987, CUR-1988 correspond to samples treated with SEQ ID NOS 14 to 22 respectively.

Results:

Real Time PCR results show that levels of IDUA mRNA in SK-N-AS cells show a trend for increased at 48 h after treatment with the antisense oligonucleotides CUR-1976, CUR1978 and CUR-1987 to human IDUA natural antisense Hs.656285 (FIG. 4).

Example 3: Extension of the Dog IDUA Potential Natural Antisense Sequence

The purpose of this experiment is to extend the known sequence of the dog IDUA natural antisense DN876121 by sequencing all its sequence. The original DN876121 RNA transcript was obtained from dog eye minus lens and cornea tissue. A directionally cloned cDNA library was prepared in a pCMVSport6 vector (Invitrogen) at Bioserve Biotechnology by Laurel MD. This work was done by April 2005. The DN876121 clone is currently available at Open Biosystems (Open Biosystems Products, Huntsville, Ala.). In April 2005, the DN876121 clone was not sequenced completely. OPKO-CURNA obtained the DN876121 clone and sequenced the full insert. To achieve this, a bacterial clone containing a plasmid with the DN876121 insert was acquired from Open Biosystems and plated in a Luria Bertani (LB)-agar plate with ampicillin to isolate individual colonies. Then colonies were amplified in S ml of LB broth. The plasmid containing the DN876121 insert was then isolated from these bacteria and sent for sequencing to Davis Sequencing (Davis, Calif.).

Material and Methods: Isolation and Sequencing of the Plasmid Containing the cDNA for the Dog IDUA Potential Natural Antisense DN876121—

Suspension of frozen bacteria containing the DN876121 plasmid was purchased from Open Biosystems (Open Biosystems Products, cat# NAE04B03), diluted 1:10, 1:100, 1:1000, 1:10000, 1:100000 times, then plated on Luria Bertani (LB) (BD, cat#244520)-agar plate (Falcon, cat#351005) with 100 µg/ml of ampicillin (Calbiochem, cat#171254). After 15 h, 20 individual colonies of bacteria were isolated from the plate with the 1:100000 dilution and grown separately in 5 ml of LB broth (Fisher Scientific, cat# BP1426-2) for 15 h-24 h. At this time, the bacteria were pelleted and the plasmid (containing the cDNA from the DN876121 RNA transcript) was isolated using the PureYield™ Plasmid Miniprep System kit from Promega (Promega, cat#A1222) following the manufacturer's protocol. The isolated DNA was diluted to 200 ng/ml and 12 µl of plasmid from each colony was sent for sequencing to Davis sequencing (Davis, Calif.).

Figure 5:
FIG. 5 (SEQ ID NO: 8) shows the extension by 578 nucleotides (gray) of the original sequence dog DN876121 sequence (SEQ ID NO: 5) (in clear) using Clone open biosystems: NAE04B03.

Results:

The sequences obtained from Davis sequencing showed a substantial extension of the known DN876121 sequence shown in FIG. 5.

Conclusion:

The successful extension of the known DN876121 sequence by 578 nucleotides served as a basis to design antisense oligonucleotides against the dog IDUA potential natural antisense transcript DN876121-extended (SEQ ID NO:8).

Example 4: IDUA Activity

The purpose of this experiment is to rank compounds according to their ability to upregulate the IDUA activity in different cells using the enzymatic activity of IDUA. This method could be used to rank oligonucleotide complementary to the IDUA natural antisense known to up-regulate the IDUA mRNA (and IDUA protein) for their capacity to increase the IDUA activity. This protocol in combination with the patient fibroblast cell expansion protocol could allow to screen in vitro for the correct oligonucleotide complementary to the IDUA natural antisense able to increase the activity of IDUA before offering this oligonucleotide as a treatment to a patient.

Materials and Methods:

Cells will be treated with oligonucleotides complementary to the IDUA natural antisense at 0 to 80 nM using Lipofectamine™ 2000. After 24 h, the medium will be discarded and fresh medium will be added for 24 h up to 72 h. At that time, the medium will be stored and checked for IDUA activity. The IDUA activity will be measured using as control recombinant human IDUA (from R&D systems Inc. Minneapolis Minn.) serial diluted (maximum concentration at 0.2 microg/mL) in assay buffer (50 mM NaOAc, 150 mMNaCl, 0.02% Brij-35 (w/v) pH3.5). An equal volume of recombinant human IDUA in assay buffer with IDUA substrate (4-methylumbelliferyl-alpha-L-iduronide) from Glycosynth (Warrington, UK) at 200 microM in assay buffer will be mixed in a 96 well plate (100 microL each reaction solution). Incubate for 10 min at room temperature Dilute the mixtures for 0.005 microg/mL maximum recombinant human IDUA (and 5 microM of substrate) in developing buffer (0.1M Tris pH9.0). Load 100 microL of the diluted reactions into a fluorescence assay plate. The solution is read at 365 nm and 445 am. The specific activity will be calculated (pmoles/min/microg) as follow:

IDUA activity=Adjusted for substrate blank Fluorescence (RFU)×Conversion factor (pmole/RFU) Incubation time (min)×amount of enzyme (microg)

The IDUA activity will be measured in cell supernatant by adding cell supernatant from cells treated with different amounts of different oligonucleotides complementary of the IDUA natural antisense transcript instead of recombinant human IDUA in this protocol.

Example 5: IDUA Protein ELISA

The purpose of this experiment is to rank compounds according to their ability to upregulate the IDUA protein expression in different cells using a technique called enzyme-linked immunosorbent assay (ELISA).

Materials and Methods:

Amounts of IDUA protein produced by the cells will be quantified by ELISA. To achieve this, the cells will be grown in 24-well plates using appropriate growth conditions. Forty eight hours after addition of small compounds, the media will be removed and the cells will be washed 3 times with Dulbecco's phosphate-buffered saline without calcium and magnesium (PBS) (Mediatech cat#21-031-CV). Then PBS will be discarded and the cells will be fixed in the 24 well plate using 100 µl of 100% methanol for 15 min at −20° C. After removing the methanol and washing with PBS, the cells will be incubated with 3% hydrogen peroxide (Fisher Chemical cat#H325-100) for 5 min at 21° C. The cells will be washed three times for 5 min with PBS, then incubated with 100 µl of bovine serum albumin (BSA) (Sigma cat# A-9647) at 0.1% in PBS for 30 min at 21° C. The cells will be washed three times for 5 min with PBS then incubated with 300 µl of avidin solution (Vector Laboratories cat# SP-2001) for 30 min at 21° C. The cells will be briefly rinsed three times with PBS then incubated with biotin solution (Vector Laboratories cat# SP-2001) for 30 min at 21° C. The cells will be washed three times with PBS and then incubated overnight at 4'C with 100 µl per well of rabbit antibody raised against a region within internal sequence amino acids 244-274 of Human IDUA (Abeam cat# ab103949) in PBS/BSA 0.1%. After equilibrating the plate for 5 min at 21° C., the cells will be washed three times for 5 min each with PBS then incubated with goat anti-rabbit antibody diluted 1:200 in PBS/BSA 0.1% for 30 min at 21° C. The cells will be washed three times for 5 min with PBS and then incubated with 300 µl of Vectastain Elite ABC reagent A+B solution (Vector Laboratories cat# PK-6101) for 30 min; the Vectastain Elite ABC reagent A+B solution will be prepared at 21° C. 30 min before incubation with the cells by adding and mixing successively 2 drops of reagent A to 5 ml of PBS and then 2 drops of reagent B. The cells will be washed 3 times for 5 min with PBS at 21° C. and then incubated with tetramethylbenzidine (TMB) peroxidase substrate solution (Thermo Scientific cat#N301). After the supernatant turns blue, it will be transferred to a new 96 well ELISA plate (Greiner bio one cat #65121) and 1 M sulfuric acid will be added. The absorbance will be read at 450 nm using a Multiskan Spectrum spectrophotometer (Thermo Scientific). The background signal, read in the wells stained with a rabbit anti-mouse IgG as primary antibody (Abeam cat#ab6709) will be subtracted from all IDUA and actin readings. Rabbit anti-actin antibody from Abcam (cat# ab1801) will be used. The IDUA signal will be normalized to actin signal for each condition and normalized values for each experimental variant will be compared.

Example 6: IDUA Immune-Histochemistry

The purpose of this experiment is to rank compounds according to their ability to upregulate the IDUA protein expression in different cells using a technique called immunohistochemistry.

Materials and Methods:

IDUA protein will be detected inside cells by immunohistochemistry. To achieve this, the cells will be grown in 24-well plates using appropriate growth conditions. Forty eight hours after addition of small compounds, the media will be removed and the cells will be washed 3 times with Dulbecco's phosphate-buffered saline without calcium and magnesium (PBS) (Mediatech cat#21-031-CV). Then PBS will be discarded and the cells will be fixed in the 24 well plate using 300 µl of 100% methanol for 15 min at −20° C. After removing the methanol and washing with PBS, the cells will be incubated with 3% hydrogen peroxide (Fisher Chemical cat#H325-100) for 5 min at 21° C. The cells will be washed three times for 5 min with PBS, then incubated with 300 µl of bovine serum albumin (BSA) (Sigma cat# A-9647) at 0.1% in PBS for 30 min at 21° C. The cells will be washed three times for 5 min with PBS then incubated with 300 µl of avidin solution (Vector Laboratories cat# SP-2001) for 30 min at 21° C. The cells will be briefly rinsed three times with PBS then incubated with biotin solution (Vector Laboratories cat# SP-2001) for 30 min at 21° C. The cells will be washed three times with PBS and then incubated overnight at 4° C. with 300 µl per well of rabbit antibody raised against a region within internal sequence amino acids 244-274 of Human IDUA (Abcam cat# ab103949) in PBS/BSA 0.1%. After equilibrating the plate for 5 min at 21° C., the cells will be washed three times 5 min each with PBS then incubated with goat anti-rabbit antibody diluted 1:200 in PBS/BSA 0.1% for 30 min at 21° C. The cells will be washed three times for 5 min with PBS and then incubated with 300 µl of Vectastain Elite ABC reagent A+B solution (Vector Laboratories cat# PK-6101) for 30 min; the Vectastain Elite ABC reagent A+B solution will be prepared at 21° C. 30 min before incubation with the cells by adding and mixing successively 2 drops of reagent A to 5 ml of PBS and then 2 drops of reagent B. The cells will be washed 3 times for 5 min each with PBS at 21° C. and then incubated with Diaminobenzidine (DAB) peroxidase substrate solution (Vector Laboratories cat# SK-4105) until cells are stained; the DAB peroxidase substrate solution will be reconstituted before being added to the cells by mixing 1 ml of ImmPACT™DAB Diluent with 30 µl of ImmPACT™ DAB Chromogen concentrate. At this time, the cells will be briefly washed three times with PBS and 300 µl of PBS will be left in each well. The staining of the cells will be analyzed directly inside the wells of the 24-well plate using an inverted Nikon Eclipse TS100 microscope equipped with a Nikon DS-Ril camera coupled with Nikon Digital-Sight equipment on the screen of a Dell Latitude D630 laptop. Photos of individual wells will be made using the software provided with the Nikon camera, the NIS-Elements D 3.0.

Example 7: Patient Fibroblasts

The purpose of this experiment is to identify the right oligonucleotide known to up-regulate IDUA mRNA in the right patient population. The IDUA mutation is also present in the patient skin fibroblast cells. By dosing such cells in vitro, it will be possible to identify which oligonucleotide complementary to the IDUA natural antisense could help patient benefit from this innovative treatment.

Materials and Methods:

A skin biopsy will be performed according to the FDA regulations and with patient consent in order to expand the patient skin fibroblasts in cell culture for in vitro testing of the oligonucleotides complementary to the IDUA natural antisense. This biopsy will be treated with collagenase in order to dissociate the skin cells and this cell suspension will be plated in wells of 6-well plates in 2 ml of Dulbecco's Modified Eagle Medium/Nutrient Mixture F-12 (Invitrogen cat#10565) with 20% Fetal Bovine Serum (from GIBO/Invitrogen Cat. #35-011CV). When the cells reach 70% confluence, they will be splited at 1:4 in 2 ml of of Dulbecco's Modified Eagle Medium/Nutrient Mixture F-12 (Invitrogen cat#10565) with 20% Fetal Bovine Serum (from GIBO/Invitrogen Cat. #354)11CV). These cells will be dosed with oligonucleotides complementary to the IDUA natural antisense following the same protocol as describe previously to check for IDUA mRNA up-regulation. The total cell RNA will be checked for up-regulation of the IDUA mRNA after dosing with oligonucleotides complementary to the IDUA natural antisense transcript. The supernatant of these cells will be checked for up-regulation of the IDUA activity after dosing with oligonucleotides complementary to the IDUA natural antisense transcript.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

What is claimed is:

1. A method of identifying and selecting at least one modified antisense oligonucleotide of 10 to 30 nucleotides in length specific for a natural antisense polynucleotide of an IDUA gene for in vivo administration comprising: identifying at least one antisense oligonucleotide comprising at least ten consecutive nucleotides which are at least 90% complementary to a natural antisense polynucleotide of the IDUA gene; measuring the thermal melting point of a hybrid of said antisense oligonucleotide and the natural antisense polynucleotide under stringent hybridization conditions; identifying said antisense oligonucleotide that specifically hybridize to said natural antisense polynucleotide and upregulate the expression of the IDUA gene relative to a control and selecting at least one oligonucleotide for in vivo administration based on the information obtained.

2. The method according to claim 1 wherein the antisense oligonucleotides are 10 to 30 nucleotides in length and are modified with at least one modification selected from the group consisting of at least one modified sugar moiety, at least one modified internucleoside linkage, at least one modified nucleotide, and combinations thereof.

3. The method according to claim 1 wherein the IDUA natural antisense polynucleotides are selected from the group consisting of nucleotides 1 to 2695 of SEQ ID NO: 2 or 1 to 2082 of SEQ ID NO: 3 or 1 to 322 of SEQ ID NO: 4 or 1 to 677 of SEQ ID NO: 5 or 1 to 716 of SEQ ID NO: 6 or 1 to 466 of SEQ ID NO: 7 or 1 to 1255 of SEQ ID NO: 8 or 1 to 2739 of SEQ ID NO: 9.

4. The method of claim 2, wherein the one or more modifications comprise at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and combinations thereof.

5. The method of claim 2, wherein the one or more modifications comprise at least one modified internucleoside linkage selected from: a phosphorothioate, 2'-Omethoxyethyl (MOE), 2'-fluoro, alkylphosphonate, phosphorodithioate, alkylphosphonothioate, phosphoramidate, carbamate, carbonate, phosphate triester, acetamidate, carboxymethyl ester, and combinations thereof.

6. The method of claim 2, wherein the one or more modifications comprise at least one modified nucleotide selected from: a peptide nucleic acid (PNA), a locked nucleic acid (LNA), an arabino-nucleic acid (FANA), an analogue, a derivative, and combinations thereof.

7. The method of claim 2, wherein the at least one oligonucleotide comprises at least one oligonucleotide sequences set forth as SEQ ID NOS: 10 to 28.

8. A method of identifying and selecting an antisense oligonucleotide of 10 to 30 nucleotides in length to treat a patient in need of treatment thereof for an IDUA related disease or disorder comprising identifying a patient having a deficiency in IDUA function; selecting cells or tissue from a patient having a deficiency in IDUA function; identifying said antisense oligonucleotides of 10 to 30 nucleotides in length that specifically hybridize to a natural antisense polynucleotide of an IDUA polynucleotide and upregulate the expression thereof relative to a control; treating said cells or tissues with a plurality of said antisesene oligonucleotides; determining the percentage increase of IDUA expression in the cells or tissues and selecting the oligonucleotide to administer to the patient.

* * * * *